(12) United States Patent
Murphy et al.

(10) Patent No.: US 8,075,562 B2
(45) Date of Patent: Dec. 13, 2011

(54) CONTROLLED RELEASE OF BIOPHARMACEUTICAL GROWTH FACTORS FROM HYDROXYAPATITE COATING ON BIORESORBABLE INTERFERENCE SCREWS USED IN CRUCIATE LIGAMENT RECONSTRUCTION SURGERY

(75) Inventors: William L. Murphy, Madison, WI (US); Jae-Sam Lee, Houston, TX (US); Mark D. Markel, Middleton, WI (US); Ben K. Graf, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 215 days.

(21) Appl. No.: 12/145,672

(22) Filed: Jun. 25, 2008

(65) Prior Publication Data

US 2009/0087472 A1 Apr. 2, 2009

Related U.S. Application Data

(60) Provisional application No. 60/937,460, filed on Jun. 25, 2007.

(51) Int. Cl.
*A61B 17/56* (2006.01)
*A61B 17/58* (2006.01)
*C07K 14/51* (2006.01)

(52) U.S. Cl. ............ 606/77; 606/53; 424/484; 424/486; 514/8.8

(58) Field of Classification Search ........................ None
See application file for complete search history.

(56) References Cited

U.S. PATENT DOCUMENTS

| | | | |
|---|---|---|---|
| 4,889,917 A | 12/1989 | Tanihara et al. | |
| 4,894,442 A | 1/1990 | Toyama et al. | |
| 5,132,402 A | 7/1992 | Tanihara et al. | |
| 5,171,837 A | 12/1992 | Tanihara et al. | |
| 5,344,654 A * | 9/1994 | Rueger et al. | 424/423 |
| 5,624,900 A | 4/1997 | Suda et al. | |
| 5,658,592 A | 8/1997 | Tanihara et al. | |
| 5,770,229 A | 6/1998 | Tanihara et al. | |
| 5,880,216 A | 3/1999 | Tanihara et al. | |
| 5,980,883 A | 11/1999 | Tanihara et al. | |
| 6,162,864 A | 12/2000 | Tanihara et al. | |
| 6,187,742 B1 * | 2/2001 | Wozney et al. | 514/2 |
| 6,541,022 B1 | 4/2003 | Murphy et al. | |
| 6,617,307 B1 | 9/2003 | Nishimura et al. | |
| 6,767,928 B1 | 7/2004 | Murphy et al. | |
| 6,916,321 B2 * | 7/2005 | TenHuisen et al. | 606/312 |
| 7,049,293 B2 | 5/2006 | Nishimura et al. | |
| 7,132,397 B1 | 11/2006 | Katsuura et al. | |
| 7,132,506 B2 | 11/2006 | Nishimura et al. | |
| 7,179,795 B2 | 2/2007 | Wiederanders et al. | |
| 7,229,441 B2 * | 6/2007 | Trieu et al. | 606/279 |
| 2002/0061837 A1 | 5/2002 | Lough et al. | |
| 2003/0007971 A1 | 1/2003 | Tanihara et al. | |
| 2003/0162941 A1 | 8/2003 | Tanihara et al. | |
| 2005/0079470 A1 * | 4/2005 | Rutherford et al. | 433/226 |
| 2006/0235204 A1 | 10/2006 | Desjarlais et al. | |
| 2007/0026437 A1 | 2/2007 | Wang et al. | |

OTHER PUBLICATIONS

Yan Lu, M.D., et al., "Comparison of Single- Versus Double-Tunnel Tendon-to-Bone Healing in an Ovine Model A Biochemical and Histological Analysis," Am. J. Sports Med. 37:512-517 (2009).
Yan Lu, M.D., et al., "Influence of Hydroxyapatite-Coated and Growth Factor-Releasing Interference Screws on Tendon-Bone Healing in an Ovine Model," Arthroscopy 25(12):1427-1435 (2009).
Anderson K et al., "Augmentation of Tendon Healing in an Intraarticular Bone Tunnel with Use of a Bone Growth Factor," Am J Sports Med 2001, 29:689-698.
Buelow Ju et al., "A New Biocortical Tibial Fixation Technique in Anterior Cruciate Ligament Reconstruction with Quadruple Hamstring Graft," Knee Surg Sports Traumatol Arthrosc 2000, 8:218-225.
Harris H et al., "Functional analysis of bone sialoprotein: identification of the hydroxyapatite-nucleating and cell-binding domains by recombinant peptide expression and site-directed mutagenesis," Bone 2000, 27:795-802.
Hoang Q et al., "Bone Recognition Mechanism of Porcine Osteocalcin form Crystal Structure," Nature 2003, 425:977-980.
Huq, N.L. et al., "The amino acid sequences of goat, pig and wallaby osteocalcins," Biochem. Int., 1984, 8(4):521-527.
Knowledge Enterprise, "The worldwide orthopedic market," The Institute for Orthopedic Enlightenment, Chagrin Falls, OH, 2003:1-60.
Lind M, "Growth Factor Stimulation of Bone Healing: Effects on osteoblasts, osteomies and implants fixation," Acta Orthop Scand Suppl 1998, 283:2-37.
Linn RM et al., "Achilles Tendon Allograft Reconstruction of Anterior Cruciate Ligament Deficient Knee," Am J Sports Med 1993, 21:825-831.
Medtech Insight, "Poor man's growth factors: do they work?," Medtech Insight Newletter, Nov./Dec. 2003:263-264.
Murphy WL et al, "Sustained Release of Vascular Endothelial Growth Factor From Mineralized poly(lactide-co-glycolide) Scaffolds for Tissue Engineering," Biomaterials 2000, 21:2521-2527.
Murphy WL et al, "Bioinspired Growth of Crystalline Carbonate Apatite on Biodegradable Polymer Substrata," J Am Chem Soc 2002, 124-1910-1917.
Murphy WL et al, "Bone Regeneration via a Mineral Substrate and Induced Angiogenesis," J Dent Res 2004, 83:204-210.

(Continued)

*Primary Examiner* — Daniel C Gamett
(74) *Attorney, Agent, or Firm* — Armstrong Teasdale LLP

(57) ABSTRACT

Controlled release of biopharmaceutical growth factors from a hydroxyapatite coating on a bioresorbable interference screw used in cruciate ligament reconstruction surgery on a human. Biologically active scaffolds, such as interference bone screws used for ligament fixation, made by growing calcium phosphate-based hydroxyapatite coatings on bioresorbable poly(α-hydroxy ester) scaffolds that provide controlled mineral dissolution and controlled release of bone morphogenetic protein-2. The biologically active scaffold provides improved bioavailability of BMP-2 growth factor that in turn provides enhanced graft-bone healing in the tibial bone tunnel. The coating method uses surface hydrolysis and modified simulated body fluid incubation which does not require solvent or heat and is conducted at room temperature.

25 Claims, 42 Drawing Sheets

OTHER PUBLICATIONS

Murphy WL et al, "Effects of a bone-like mineral film on phenotype of adult human mesenchymal stem cells in vitro," Biomaterials 2005, 26:303-310.

Rodeo SA et al., "Use of Recombinant Human Bone Morphogenetic Protein-2 to Enhance Tendon Healing in a Bone Tunnel," Am J Sports Med 1999, 27:476-488.

Saito A et al., "Activation of osteo-progenitor cells by a novel synthetic peptide derived from the bone morphogenetic protein-2 knuckle epitope," Biochimica et Biophysica Acta 2003, 1651:60-67.

Saito A et al., "Prolonged ectopic calcification induced by BMP-2-derived synthetic peptide," Journal of biomedical materials research. Part A 2004, 701:115-121.

Seeherman H, "The Influence of Delivery Vehicles and Their Properties on the Repair of Segmental Defects and Fractures with Osteogenic Factors," J Bone Joint Surg Am 2001, 83A Suppl. 1:S79-81.

Sheridan M et al., Bioabsorbable polymer scaffolds for tissue engineering capable of sustained growth factor delivery,: J. Cvontrol Release 2000, 64:94-102.

Tye C et al., "Dilineation of the hydroxyapatite-nucleating domains of bone sialoprotein," J. Biol. Chem. 2003, 278:7949-7955.

Winn S et al., "Sustained Release Emphasizing Recombinant Human Bone Morphogenetic Protein-2," Adv Drug Deliv Rev 1998, 31:303-318.

* cited by examiner

CONTROLLED RELEASE OF BIOPHARMACEUTICAL GROWTH FACTORS FROM HYDROXYAPATITE COATING ON BIORESORBABLE INTERFERENCE SCREWS USED IN CRUCIATE LIGAMENT RECONSTRUCTION SURGERY

CROSS-REFERENCE TO RELATED APPLICATIONS

The application claims the benefit of U.S. Provisional Application No. 60/937,460 filed on Jun. 25, 2007. This application is incorporated herein by reference as if set forth in its entirety.

STATEMENT REGARDING FEDERALLY SPONSORED RESEARCH OR DEVELOPMENT

This invention was made with United States Government support awarded by the following agency: NIH AR052893. The United States Government has certain rights in this invention.

BACKGROUND

Costs of musculoskeletal conditions represent an average of 3% of the gross domestic product of developed countries, which consumes an estimated $254 billion annually in the U.S. In addition, the U.S. market segment for orthopedic implants is around $100 million and growing.

Regeneration of natural skeletal tissue represents a promising new approach to expand the range of conditions that can be effectively treated. Investigators have developed various biomaterial-based approaches to direct bone regeneration. However, shortcomings concerning the creation of new tissue regeneration approaches have slowed translation of new technologies from the laboratory to the clinic.

Regeneration of skeletal tissues is an active area of study in academia and industry. Revenues for bone growth therapeutic products are expected to grow by more than 40% per year for the foreseeable future. (Medtech Insight, "Poor man's growth factors: do they work?," *Medtech Insight Newsletter*, November/December 2003:263-264).

Costs for musculoskeletal conditions may represent an average of 3% of the GDP of some developed countries, which may consume an estimated $254 billion annually. For example, in the U.S. bone and joint disease account for half of all chronic conditions in people over the age of 50. (Knowledge Enterprise, "the worldwide orthopedic market," *The Institute for Orthopedic Enlightenment*, Chagrin Falls, Ohio, 2003:1-60). This age group may also double in population by 2020, which suggests a tremendous rapidly growing need for new and effective bone repair/replacement therapies.

Such new and effective therapies (designed to induce bone regeneration in skeletal defects or injuries) have been limited by the need for efficient and effective targeted and controlled delivery of therapeutic drug molecules locally within the body. Compatibility with conventional standard surgical techniques and procedures has also limited implementation of various therapies.

Various "inductive" molecules are able to stimulate bone regeneration, however, efficient targeted and controlled delivery of such therapeutic inductive molecules remains problematic. Others have reported development of a gas foaming polymer process providing fabrication of three-dimensional porous matrices from bioabsorbable materials, whereby angiogenic factors were subsequently incorporated into the matrices during the fabrication process, and the angiogenic factors are released in a controlled manner. (Sheridan M, et al., "Bioabsorbable polymer scaffolds for tissue engineering capable of sustained growth factor delivery," *J. Control. Release* 2000, 64:94-102).

There still exists a need to provide drug delivery platforms, dosage forms, compositions, methods and devices thereof capable of delivering inductive molecules in a targeted and controlled fashion having suitable bioavailability.

In addition, use of new tissue regeneration approaches by clinicians has been troublesome because they are often not designed for facile translation into existing surgical procedures, which renders such approaches impractical.

The instant invention advantageously overcomes the problems and needs set forth herein.

BRIEF SUMMARY

One aspect of the invention is related to controlled release of biopharmaceutical growth factors from a hydroxyapatite coating on a bioresorbable interference screw used in cruciate ligament reconstruction surgery on a human.

One aspect of the invention is a method of growing hydroxyapatite on a bioresorbable substrate, the hydroxyapatite having one or more active biopharmaceutical growth factors chemically bonded therein, comprising the steps or acts of surface hydrolyzing the bioresorbable substrate under alkaline conditions, and, incubating the hydrolyzed bioresorbable substrate in modified simulated body fluid containing calcium ions, phosphate ions and growth factor.

In an exemplary embodiment of the method, the bioresorbable substrate is constructed from a poly(α-hydroxy ester).

In another exemplary embodiment of the method, the poly (α-hydroxy ester) is a poly(L-lactide), poly(lactide-co-glycolide) or poly(ε-caprolactone).

In another exemplary embodiment of the method, the poly (α-hydroxy ester) is poly(L-lactide).

In another exemplary embodiment of the method, the active biopharmaceutical growth factor includes a first polypeptide being SEQ ID NO: 2, amino acids 299-396 of SEQ ID NO: 2, amino acids 283-396 of SEQ ID NO: 2, SEQ ID NO: 5, SEQ ID NO: 6, SEQ ID NO: 7, SEQ ID NO: 14, SEQ ID NO: 15, SEQ ID NO: 16, SEQ ID NO: 17, SEQ ID NO: 18 or SEQ ID NO: 19.

In another exemplary embodiment of the method, the active biopharmaceutical growth factors includes a second polypeptide being SEQ ID NO: 4, amino acids 311-408 of SEQ ID NO:4 or amino acids 293-408 of SEQ ID NO: 4.

In another exemplary embodiment of the method, the bioresorbable substrate is an interference screw.

Another aspect of the invention is an interference screw made by any of the above methods.

Another aspect of the invention is an implantable scaffold made by any of the above methods.

Another aspect of the invention is a method of reconstructing anterior cruciate ligament in a human comprising the steps or acts of removing damaged ligament, drilling a tunnel through the tibia and femur, inserting a graft selected from the group consisting of hamstring tendon and patellar tendon through the tibia tunnel and the femur tunnel, affixing the graft to tibia and femur tunnels with the interference screw made by any of the above methods.

Another aspect of the invention is a method of treating or reducing tunnel widening in the tibia or femur of a patient attendant to reconstruction of the anterior cruciate ligament in a human comprising the steps or acts of controlled delivery of growth factor from any one of the above interference screws to a tendon graft secured in the tunnel by the interference screw.

Another aspect of the invention is an orthopedic implant for controlled delivery of one or more active biopharmaceutical growth factors comprising a bioresorbable scaffold, and, a bioactive coating containing calcium, phosphate, and one or more active biopharmaceutical growth factors.

In an exemplary embodiment of the orthopedic implant, the bioresorbable scaffold is constructed from a poly(α-hydroxy ester).

In an exemplary embodiment of the orthopedic implant, the poly(α-hydroxy ester) is a poly(L-lactide), poly(lactide-co-glycolide) or poly(ε-caprolactone).

In an exemplary embodiment of the orthopedic implant, the poly(α-hydroxy ester) is poly(L-lactide).

In another exemplary embodiment of the orthopedic implant, the scaffold is an arrow, barb, tack, anchor, nail, pin, screw, staple and plate.

In another exemplary embodiment of any one of the above orthopedic implants, the bioactive coating comprises hydroxyapatite, and the active biopharmaceutical growth factors comprise a first polypeptide being human bone morphogenetic protein-2 or a functional derivative thereof.

In another exemplary embodiment of any one of the above orthopedic implants, the first polypeptide is SEQ ID NO: 2, amino acids 299-396 of SEQ ID NO: 2, amino acids 283-396 of SEQ ID NO: 2, SEQ ID NO: 5, SEQ ID NO: 6, SEQ ID NO: 7, SEQ ID NO: 14, SEQ ID NO: 15, SEQ ID NO: 16, SEQ ID NO: 17, SEQ ID NO: 18 or SEQ ID NO: 19.

In another exemplary embodiment of any one of the above orthopedic implants, the active biopharmaceutical growth factors includes a second polypeptide being human bone morphogenetic protein-4 having the sequence of SEQ ID NO: 4, amino acids 311-408 of SEQ ID NO: 4 or amino acids 293-408 of SEQ ID NO: 4.

Another aspect of the invention is a polypeptide comprising a first amino acid sequence being amino acids 5-13 of SEQ ID NO: 8, amino acids 5-13 of SEQ ID NO: 9, amino acids 5-13 of SEQ ID NO: 10, amino acids 5-13 of SEQ ID NO: 1, amino acids 5-13 of SEQ ID NO: 12 or amino acids 5-13 of SEQ ID NO: 13. Preferably, the amino acid sequence is amino acids 5-13 of SEQ ID NO: 8, amino acids 5-13 of SEQ ID NO: 9 or amino acids 5-13 of SEQ ID NO: 10. Alternatively, the polypeptide comprises an amino acid sequence being SEQ ID NOS: 8-13. Preferably, the amino acid sequence is SEQ ID NOS: 8-10. Preferably, the polypeptide comprises 30 or fewer amino acids in length. Alternatively, the polypeptide further comprises a second amino acid sequence being SEQ ID NO: 2, amino acids 299-396 of SEQ ID NO: 2, amino acids 283-396 of SEQ ID NO: 2, SEQ ID NO: 4, amino acids 311-408 of SEQ ID NO: 4, amino acids 293-408 of SEQ ID NO: 4, SEQ ID NO: 5, SEQ ID NO: 6 or SEQ ID NO: 7. Alternatively, the polypeptide consists of the amino acid sequence.

In an exemplary embodiment, where the first amino acid sequence of the polypeptide comprises an amino acid sequence selected from SEQ ID NOS: 8-13, the polypeptide may further comprise a second amino acid sequence being SEQ ID NO: 2, amino acids 299-396 of SEQ ID NO: 2, amino acids 283-396 of SEQ ID NO: 2, SEQ ID NO: 4, amino acids 311-408 of SEQ ID NO: 4, amino acids 293-408 of SEQ ID NO: 4, SEQ ID NO: 5, SEQ ID NO: 6 or SEQ ID NO: 7. Preferably, the polypeptide consists of the amino acid sequence. Alternatively, the polypeptide consists of the first and the second amino acid sequences.

Another aspect of the invention is an isolated nucleic acid comprising a nucleotide sequence or its complement wherein the nucleotide sequence encodes any one of these polypeptides.

In an exemplary embodiment of the isolated nucleic acid, the isolated nucleic acid further comprises a promoter operably linked to the uninterrupted nucleotide coding sequence. Another aspect of the invention is a host cell comprising this isolated nucleic acid.

Another aspect of the invention is a human bone morphogenetic protein-2 molecule having the sequence of SEQ ID NO: 1, SEQ ID NO: 2, SEQ ID NO: 5, SEQ ID NO: 6 or SEQ ID NO: 7 further having the sequence of SEQ ID NO: 13.

Another aspect of the invention is an orthopedic implant for controlled delivery of growth factor comprising a bioresorbable scaffold, and, a bioactive coating comprising calcium, phosphate and any one of the above human bone morphogenetic protein-2 polypeptide molecules.

DETAILED DESCRIPTION OF THE EXEMPLARY EMBODIMENTS

Figure 1:
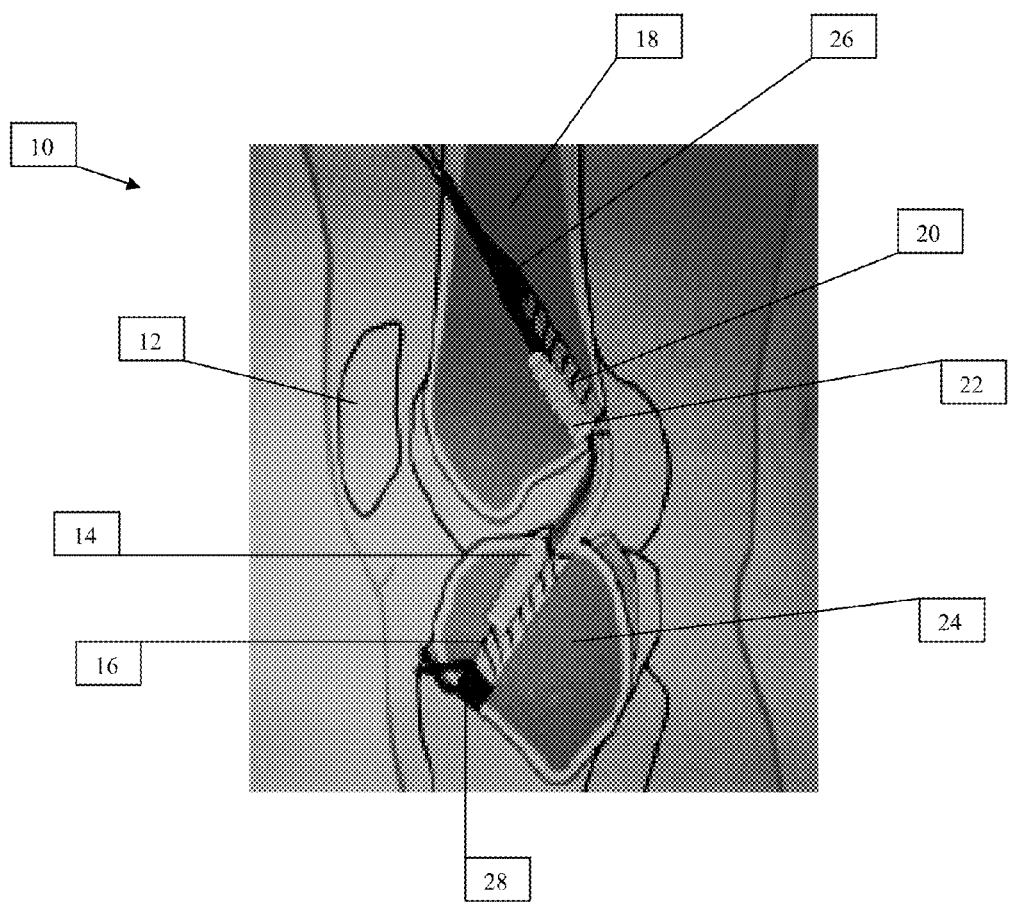
FIG. 1 shows a human knee after cruciate ligament reconstruction surgery, whereby interference bone screws provide fixation of tendon grafts within bone tunnels.
Figure 2:
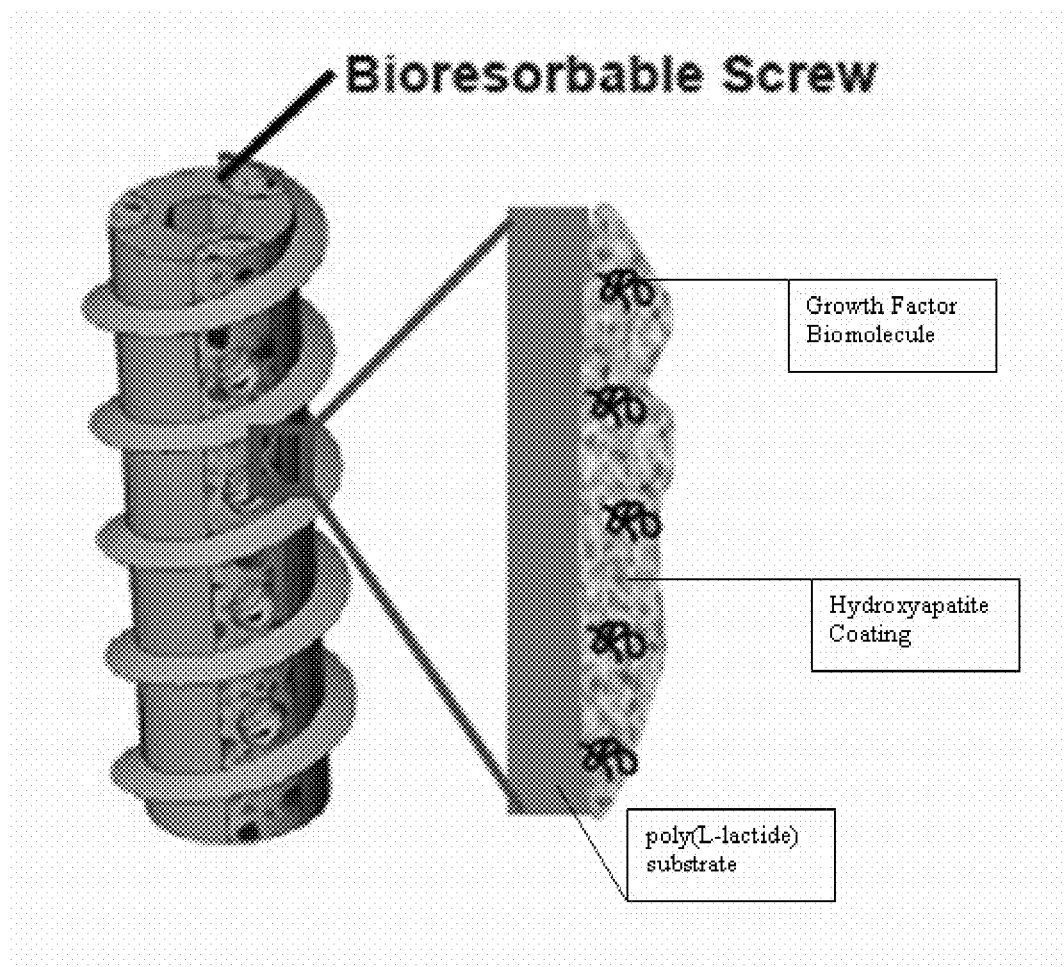
FIG. 2 shows a bioresorbable interference bone screw, whereby the cut-away cross-section shows the hydroxyapatite $\{Ca_{10}(PO_4)_6(OH)_2\}$ coating having incorporated therein growth factor biomolecules.

The instant invention includes a biologically active coating on the surface of various orthopedic implants. As used herein, one aspect of the invention is a combination implantable orthopedic medical device capable of targeted and controlled drug delivery characterized by a "biologically active coating on orthopedic implants," which is referred to as "BAC-OI."

The biologically active coating provides targeted and controlled delivery of a growth factor molecule capable of inducing bone regeneration in a mammal, preferably a human. Surgical implantation of the BAC-OI also provides for the controlled drug delivery that is targeted locally. The BAC-OI can also be advantageously implanted like any other orthopedic implant using standard orthopedic surgery techniques.

In a exemplary embodiment, the BAC-OI is utilized in cruciate ligament fixation surgery. Over 239,000 cruciate ligament reconstruction surgeries are performed in the U.S. annually, and poor graft-bone healing is a significant clinical problem associated with conventional orthopedic screw implants. The instant BAC-OI advantageously overcomes such poor graft-bone healing problems.

In an exemplary embodiment, the BAC-OI includes coating the surface of commonly-used bioresorbable orthopedic implant device (such as bone screws) with a calcium phosphate (CaP) based mineral layer, whereby the layer is adapted to contain/bind one or more therapeutic growth factors each suitable for inducing bone regeneration. Such containment is adapted to provide targeted and controlled release of the one or more therapeutic growth factors by way of mineral dissolution of the mineral layer. The CaP mineral layer is uniquely compatible with bioresorbable and provides enabling technology for targeted and controlled release of growth factors from bioresorbable orthopedic implants, particularly cruciate ligament screws.

Incorporation of engineered growth factors into CaP-based materials is disclosed in U.S. Pat. No. 6,767,928, which is incorporated herein by reference as if set forth in its entirety.

The CaP material of the instant invention may be any suitable coating material containing calcium and phosphate, such as hydroxyapatite (HAP), α-tricalcium phosphate (α-TCP), β3-tricalcium phosphate (β3-TCP), amorphous calcium phosphate, dicalcium phosphate, octacalcium phosphate, calcium carbonate and the like.

The CaP mineral layer may also include a plurality of layers having distinct dissolution profiles to control dissolution order, kinetics and other drug delivery properties. Under physiological conditions, solubility of calcium phosphate materials are as follows:

Amorphous calcium phosphate>dicalcium phosphate>octacalcium phosphate>β-TCP>HAP. A dicalcium phosphate mineral typically has a dissolution rate more than 50× higher than HAP. Thus, a plurality of various CaP layers provides a broad range of dissolution patterns. Incorporation of blank layers (i.e., CaP layers not containing any growth factor or drug) provides for delayed release.

"Orthobiologics" therapy may employ inductive molecules (e.g., growth factors) to promote natural bone growth in skeletal defects. Delivery of orthobiologics to bone defects has involved embedding or adsorbing proteins within collagen sponges, porous ceramic blocks, or synthetic polymers, which has been successful in healing segmental bone defects in animal models. (Lind M, *Acta Orthop Scand Suppl* 1998, 283:2-37; and Seeherman H, *J Bone Joint Surg Am* 2001, 83A Suppl. 1, S79-81). Clinical trials are investigating maxillofacial surgery, non-union fractures, spine fusion, and other applications. (Hollinger J O, et al., *Adv Drug Deliv Rev* 1998, 31:303-318).

However, clinical use of orthobiologics technology has been problematic. Carrier materials used to deliver bone growth factors have been inappropriate for orthopedic applications due at least in part to poor bulk mechanical properties. In addition, diffusion of growth factors from such carrier materials has been too quick leading to rapid degradation in vivo. For example, $t^{1/2}$ of bone morphogenetic protein is approximately 2~24 hr, which yields limited bioavailability.

In contrast, the half-life ($t^{1/2}$) of instant BAC-OI is around 12 hr. to several months providing suitable therapeutic bioavailability. Bulk properties of the BAC-OI are unaffected by the growth factor-containing CaP coating. The diffusing growth factor is also protected from degradation until being released from the biodegradable CaP coating. The half-life of the coating is dependent on the coating thickness and the environment, whereby coating degrades via both cell-mediated and non cell-mediated mechanisms. The range of half-lives from 12 hours to several months reasonably depends upon the circumstances. A dissolution analysis in simple buffer solution (Tris buffer, pH=7.4, 150 mM NaCl) indicates that a coating grown for 5 days on a poly(lactide-co-glycolide) film substrate has a half-life of approximately 7 days.

Bone morphogenetic proteins (BMPs) are an exemplary class of growth factors suitable for use in the present invention. Functional derivatives of a BMP that retain the function of the BMP are also suitable for use in the present invention. Such functional derivatives include BMPs with one or more mutations (substitution, insertion, or deletion) and fragments of BMPs with or without mutations. Others have discussed BMPs therapeutic activity to promote the formation and regeneration of bone and cartilage, as well as other biological activities. (Saito A, et al., "Activation of osteo-progenitor cells by a novel synthetic peptide derived from the bone morphogenetic protein-2 knuckle epitope," *Biochimica et Biophysica Acta* 2003, 1651:60-67, and Saito A, et al., "Prolonged ectopic calcification induced by BMP-2-derived synthetic peptide," *Journal of biomedical materials research. Part A* 2004, 701:115-21).

In an exemplary embodiment of the instant invention, the BMP growth factor contained within the CaP layer is bone morphogenetic protein-2 (BMP-2) or BMP-4 protein. In an exemplary embodiment, the BMP growth factor contained within the CaP layer is purified mature human BMP-2 protein, purified mature human BMP-4 protein or a mixture/combination thereof. The sequence for purified mature human BMP-2 (and the method of producing it by culturing a transformed cell) is shown in US Patent Application Publication No. 2007/0026437 at SEQ ID NO: 4 (e.g., amino acids 299-396 or 283-396 of SEQ ID NO: 4). The sequence for purified mature hBMP-4 (and the method of producing it by culturing a cell) is also shown in US Patent Application Publication No. 2007/0026437 at SEQ ID NO: 6 (e.g., amino acids 311-408 or 293-408 of SEQ ID NO: 4). US Patent Application Publication No. 2007/0026437 is incorporated herein by reference as if set forth in its entirety.

In another exemplary embodiment, the BMP growth factor may be any one of the various peptide variants derived from BMP disclosed in Saito A, et al., *Biochimica et Biophysica Acta* 2003, 1651:60-67 (P2-P4, see SEQ ID NOS: 5-7 in Example 9 below) and U.S. Pat. No. 7,132,506, each of which is incorporated herein by reference as if set forth in its entirety.

In one exemplary embodiment, a growth factor binds to the calcium phosphate (CaP) based mineral layer through a tag capable of binding to CaP. An example of such a tag that is capable of binding to hydroxyapatite is a peptide with an amino acid sequence of amino acids 5-13 of SEQ ID NO: 8. A growth factor can be linked to this tag for binding to hydroxyapatite. In this regard, a spacer of 1 to 20, preferably 2 to 10, and more preferably 3 to 8 amino acids can be provided between the tag and the growth factor. SEQ ID NO: 8 is an example of such a tag with a spacer of four alanines at the N-terminal end of the tag. Various other tags with varying binding capabilities are provided in SEQ ID NOS: 9-13 along with four alanines as a spacer at the N-terminal end.

The invention also relates to a polypeptide comprising an amino acid sequence selected from amino acids 5-13 of any one of SEQ ID NOS: 8-13. A full length osteocalcin protein is specifically excluded from the polypeptide of the present invention. The polypeptide may be shorter than 31, 26, 21, 18, 16, 15 or 14 amino acids. Preferably, the amino acid sequence is at the N- or C-terminus of the polypeptide. It is well known in the art that the amino acids within the same conservative group can typically substitute for one another without substantially affecting the function of a protein. Therefore, said amino acid sequence in the polypeptide can have one or more conservative substitutions so long as the substituted amino acid sequence retains the function of binding to CaP. In this regard, the substituted sequence should contain at least one E, preferably at least one γE (gamma carboxylated glutamic acid; Gla). For the purpose of the present invention, such conservative groups are set forth in Table 1 below.

TABLE 1

Conservative Substitution.

| Original Residue | Conservative Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

In one embodiment, the amino acid sequence is amino acids 5-13 of one of SEQ ID NOS: 8-10. In another embodiment, the amino acid sequence is any one of SEQ ID NOS: 8-13. In still another embodiment, the amino acid sequence is any one of SEQ ID NOS: 8-10.

In one form, the polypeptide of the invention comprises a first amino acid sequence as described above and a second non-osteocalcin amino acid sequence of interest, whereby such non-osteocalcin amino acid sequence does not comprise any 10, 15, 20, 25 or 30 consecutive amino acids of an osteocalcin protein such as a porcine osteocalcin protein. In one embodiment, the non-osteocalcin amino acid sequence is that of a growth factor such as a BMP sequence or a functional derivative thereof described above.

As used herein, any reference to a "polypeptide" includes an isolated polypeptide.

The invention also relates to an isolated nucleic acid that contains an uninterrupted nucleotide coding sequence or its complement, whereby the uninterrupted coding sequence encodes a polypeptide of the invention described above.

Any nucleic acid of the invention may be provided in a vector in a conventional manner. The vector may be a cloning vector or an expression vector. As regards the expression vector, the nucleotide coding sequence is under the transcriptional control of one or more non-native expression control sequences that may include a promoter not natively found adjacent to the coding sequence such that the encoded polypeptide or protein may be produced when the vector is provided in a compatible host cell. Preferably, the host cell is a mammalian cell (and more preferably a human cell) comprising a vector containing an instant nucleic acid of the invention. The invention also includes a host cell having an instant nucleic acid integrated into its genome, whereby the nucleic acid is operably linked to a non-native expression control sequence (e.g., a promoter).

The term "isolated nucleic acid" or "isolated polypeptide" used herein means a nucleic acid or polypeptide isolated from its natural environment or prepared using synthetic methods such as those known to one of ordinary skill in the art. Complete purification is not required in either case. The nucleic acids or polypeptides of the invention can be isolated and purified from normally associated material in conventional ways such that in the purified preparation the nucleic acid or polypeptide is the predominant species in the preparation. At the very least, the degree of purification is such that the extraneous material in the preparation does not interfere with use of the nucleic acid or polypeptide of the invention in the manner disclosed herein. The nucleic acid or polypeptide is preferably at least about 85% pure, more preferably at least about 95% pure and most preferably at least about 99% pure. Further, an isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

The bioresorbable polymeric material of the instant invention may be any material suitable for various orthopedic implant devices, particularly biocompatible, non-degradable ceramic scaffolds. Such scaffolds include commonly-used or commercially-available devices, such as bioresorbable arrows, barbs, tacks, bone anchors and other anchors, nails, pins, interference screws and other screws, staples, plates and other scaffolds. A particular exemplary scaffold is an interference screw constructed from poly(L-lactide) (PLLA).

As is understood in the art, arrows, barbs and tacks are used for labrum-glenoid rim re-attachment or torn meniscus repair. The bone anchor is used for soft tissue attachment in shoulder ligament reconstruction. The interference screw is used for fixation of the cruciate ligaments of the knee. Nails and screws are used for fracture fixation of small joints of the ankle, foot or hand. Pins are used to hold bone fragments in non-load bearing applications, and staples are used for semitendonitis tendon in cruciate ligament replacement procedures.

In particular, commercially available bioresorbable interference screw products include the following: Sheathed bio-interference PLLA screw for PCL fixation from Anthrex; Bio-Cortical interference screw for fixation of soft tissue grafts in low bone density also from Arthrex; Gentle threads interference screws for blunt thread design to help protect grafts from Biomet; BiLok ACL screw that is a cannulated PLLA/TCP screw for cruciate fixation from Biocomposites; Biosteon wedge interference screw that is a cannulated screw for hamstring graft fixation also from Biocomposites; Bio-Screw/Endopearl/Smartscrew which is a polymeric bioresorbable interference screw from Linvatec; Phantom Soft-Thread screw which is a PLLA screw for soft tissue fixation of ACL grafts from Johnson & Johnson; BioRCI Bioabsorbable Screw which is a cannulated PLLA screw for cruciate fixation from Smith & Nephew; BioRCI HA Enhanced Screw which is a PLLA screw reinforced with HA for cruciate fixation also from Smith & Nephew; and Calaxo Osteoconductive Screw which is a PLA/PGA/$CaCO_3$ composite for cruciate fixation also from Smith & Nephew.

Thus, the instant BAC-OI technology advantageously serves as a universal platform for a variety of orthopedic specialties and general uses, particularly cruciate ligament fixations screws.

As shown in FIG. 1, during cruciate ligament reconstruction surgery in a human knee 10 having a patella 12 (i.e., ACL surgery) a tunnel 26 is drilled in the femur 18, and a tendon graft 20 is inserted into the tunnel 26 and secured using an interference screws 22. Similarly, a tunnel 28 is drilled in the tibia 24, and a tendon graft 16 is inserted into the tunnel 28 and secured with an interference screw 14. Growth of healthy, new bone to secure the tendon during healing requires osteogenic cells, which need a biocompatible scaffold onto which they can attach and proliferate. ACL reconstruction generally involves 4 acts or steps: Removal of the damaged ligament; drilling of tunnels through the tibia and the femur for graft positioning; placement of a hamstring tendon or patellar tendon graft into these bone tunnels; and fixation of the graft with interference screws, which minimizes graft motion in the femoral and tibial tunnels. Although successful in enhancing knee stability, the process of cruciate ligament reconstruction is plagued by significant limitations.

For example, in the absence of screw fixation, tunnel widening occurs in 75% of patients, whereby the femoral tunnels had widened 60% 30 months after surgery. (Linn R M, et al., *Am J Sports Med* 1993, 21:825-831). It has also been reported that even with screw fixation of a tendon graft, the femoral and tibial tunnel areas increased by 102% and 85%, respectively, 12 months after surgery. (Buelow J U, et al., *Knee Surg Sports Traumatol Arthrosc* 2000, 8:218-225). Such tunnel widening is indicative of bone resorption instead of the desired graft-bone healing, which creates major reconstruction challenges in cases that require revision surgery (5-10% of cases).

Another limitation of current cruciate ligament reconstruction is the excessive amount of time required for full patient recovery, which is typically around 6 months. The combination of tunnel widening and excessive recovery duration significantly increases patient trauma and loss of activity. It has been reported that bolus delivery of bone growth factors within tibial tunnels yields no tunnel widening and rapid/complete graft-bone healing, which suggest that growth factor delivery could treat, prevent, alleviate and/or reduce tunnel widening while also reducing the duration of recovery. (Rodeo S A, et al, *Am J Sports Med* 1999, 27:476-488; and Anderson K, et al., *Am J Sports Med* 2001, 29:689-698).

The instant BAC-OI in the form of bioresorbable interference screw locally delivers bone growth factors directly into the femoral and tibial tunnels, which substantially decreases bone tunnel widening, improves graft-bone healing and decreases patient suffering and inconvenience.

EXAMPLE 1

Growing continuous/contiguous CaP coatings on bioresorbable bone screws. The example will demonstrate controlled CaP mineral growth on poly(L-lactide) interference screws; demonstrate controlled mineral dissolution; and characterize composition, phase, morphology, and continuity of the mineral coating.

EXAMPLE 2

Another example will demonstrate incorporation of growth factors into CaP coatings on resorbable bone screws. The example will demonstrate controlled incorporation/release of bone morphogenetic protein-2 (BMP-2) to/from the CaP coating; confirm bioactivity of released BMP-2; and characterize initial efficacy of biologically active bone screws in a sheep ligament reconstruction model, which is predictable model for human ACL reconstruction. (See, Markel M, et al., Protocol #V1243: "Histologic and Biomechanical Comparison of Suspensory and Aperture Fixation of Tendons within a Tibial Bone Tunnel in a Sheep Model"). The example will also demonstrate enhanced graft-bone healing in a sheep tibial bone tunnel. The example will also show that the instant bioactive screws can be included in standard clinical surgical procedures.

EXAMPLE 3

Mineral growth on bioresorbable polymers. A method for growing mineral coatings on poly(α-hydroxy ester) materials, including poly(L-lactide), poly(lactide-co-glycolide), and poly(r-caprolactone). (See, Murphy W L, et al., *Biomaterials* 2000, 21:2521-2527; Murphy W L, et al., *J Am Chem Soc* 2002, 124:1910-1917; Murphy W L, et al., *J Dent Res* 2004, 83:204-210; and Murphy W L, et al., *Biomaterials* 2005, 26:303-310). The method does not require solvent or heat, which is advantageous. The method is conducted at room temperature.

Figure 3:
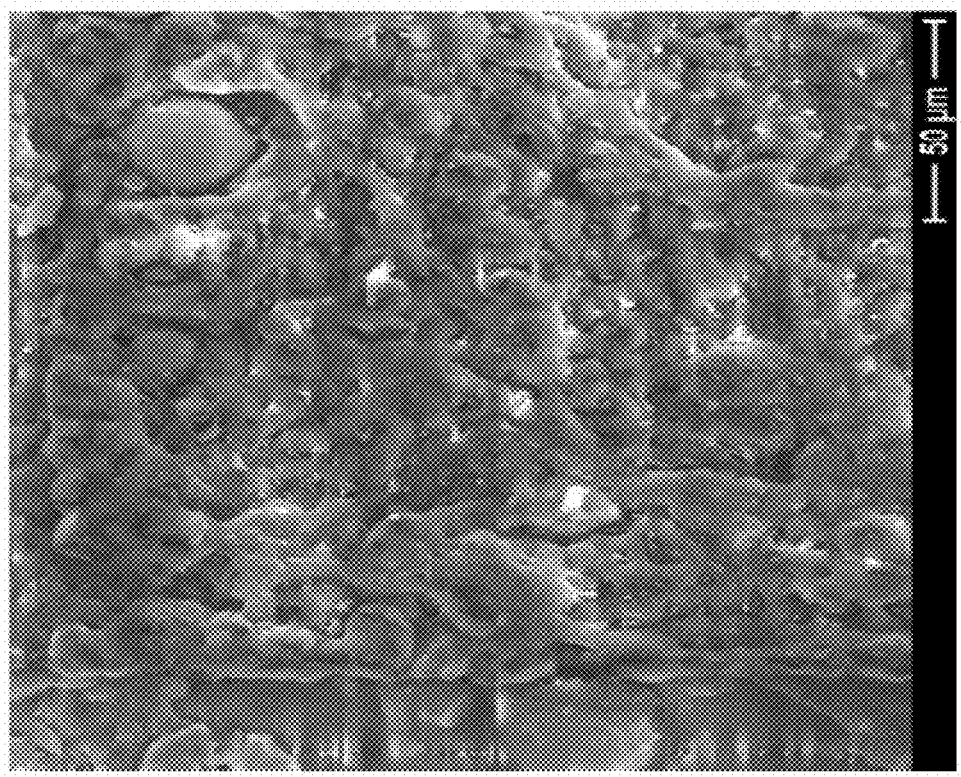
FIG. 3 is a scanning electron microscope (SEM) picture of the untreated surface of an interference bone screw constructed from resorbable poly(L-lactide).
Figure 4:
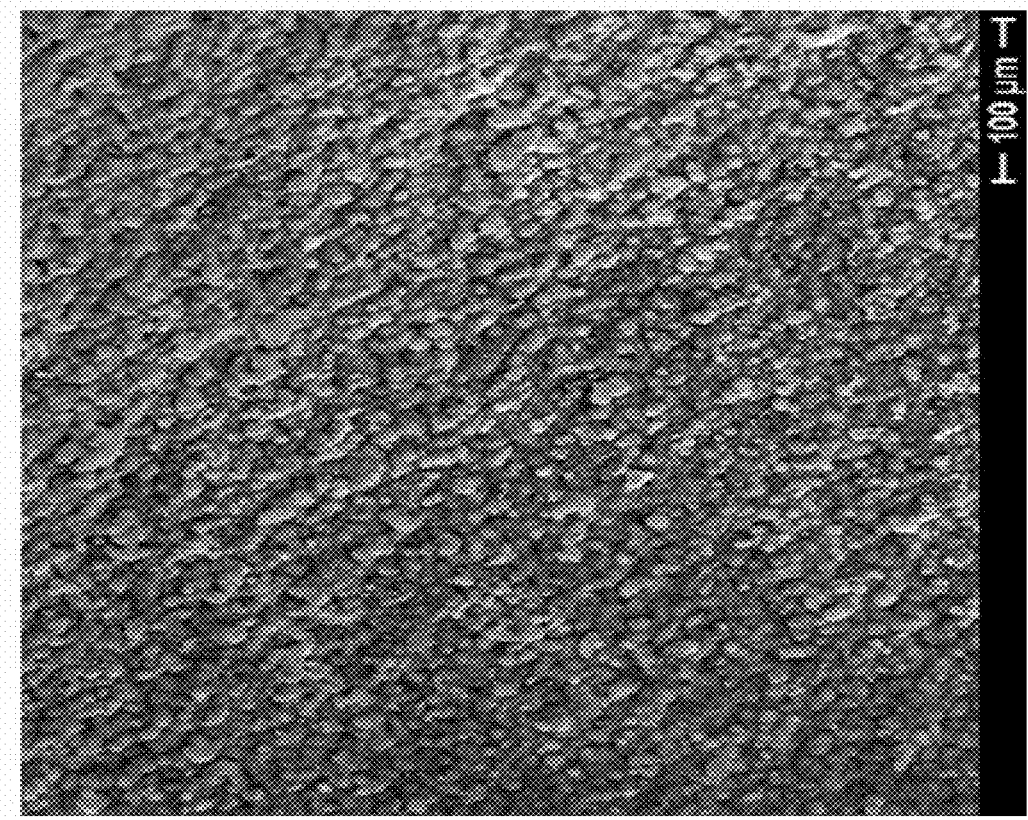
FIGS. 4 and 5 are SEM pictures of the surface of an interference bone screw constructed from resorbable poly(L-lactide) coated with a layer of hydroxyapatite.
Figure 5:
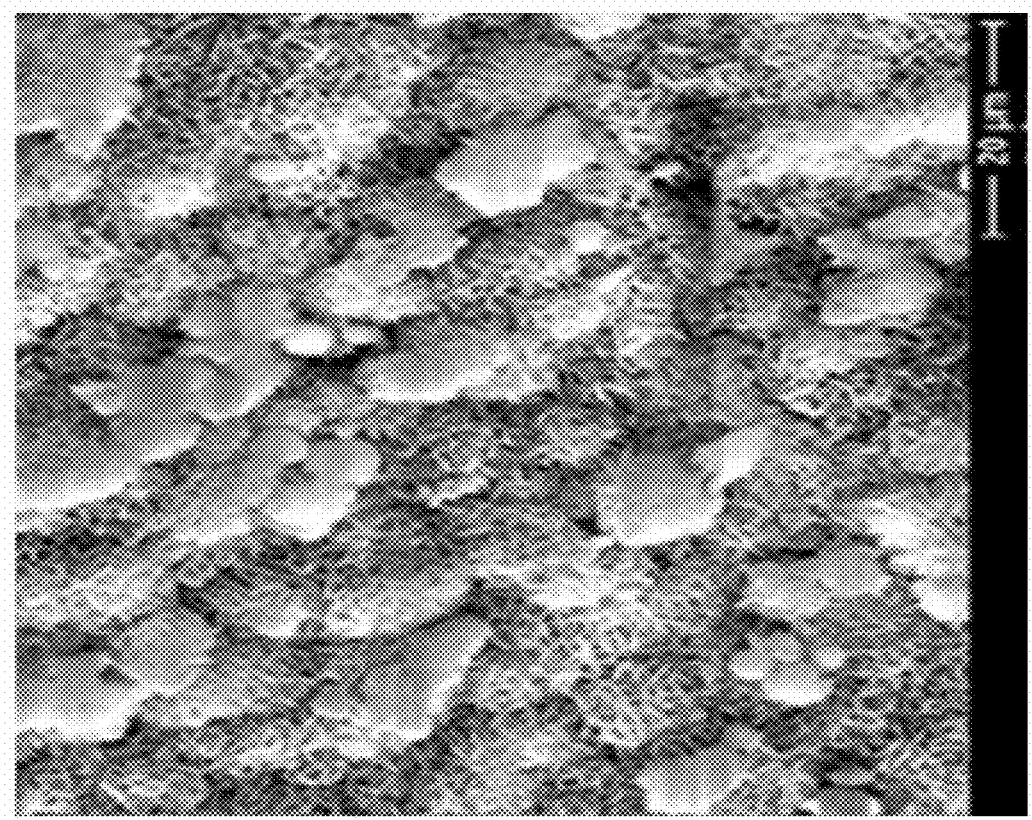

Grow continuous calcium phosphate (CaP) coatings on bioresorbable bone screws using surface hydrolysis and mSBF incubation. To induce formation of CaP-based mineral layer, PLLA interference screws (Smith & Nephew, Inc.) will be surface hydrolyzed via a 30 min. treatment in 0.1M NaOH, followed by incubation in a modified simulated body fluid (mSBF) for mineral nucleation and growth. The mSBF solution contains the ionic constituents of blood plasma, with double the concentrations of calcium and phosphate ions, and it is held at physiologic temperature and pH 6.8. Growth of CaP-based minerals, specifically bone-like minerals, on bioresorbable polymer matrices may be conducted using surface hydrolysis and mSBF incubation. (See, FIGS. 3-5).

Mineral coatings will be dissolved and analyzed for Ca and P ion content to quantify mineral formation. Mineral crystals will be analyzed morphologically and compositionally using a scanning electron microscope with a Noran SiLi detector for elemental analysis. The chemical composition will be further analyzed using Fourier transform infrared spectroscopy and x-ray diffraction. The dissolution of mineral layers will also be characterized by measuring release of Ca and P ions during incubation in tris-buffered saline at 37° C. at pH 7.4. Ca and P ion concentrations will be measured using calorimetric assays consistent with FDA's guidelines for design and testing of CaP coatings.

Growth and dissolution of the CaP coatings can be controlled, and their presence significantly increases bone regeneration in cranial defects in rats. The PLLA screw described herein is constructed from the poly(α-hydroxy ester)material.

EXAMPLE 4

Figure 10:
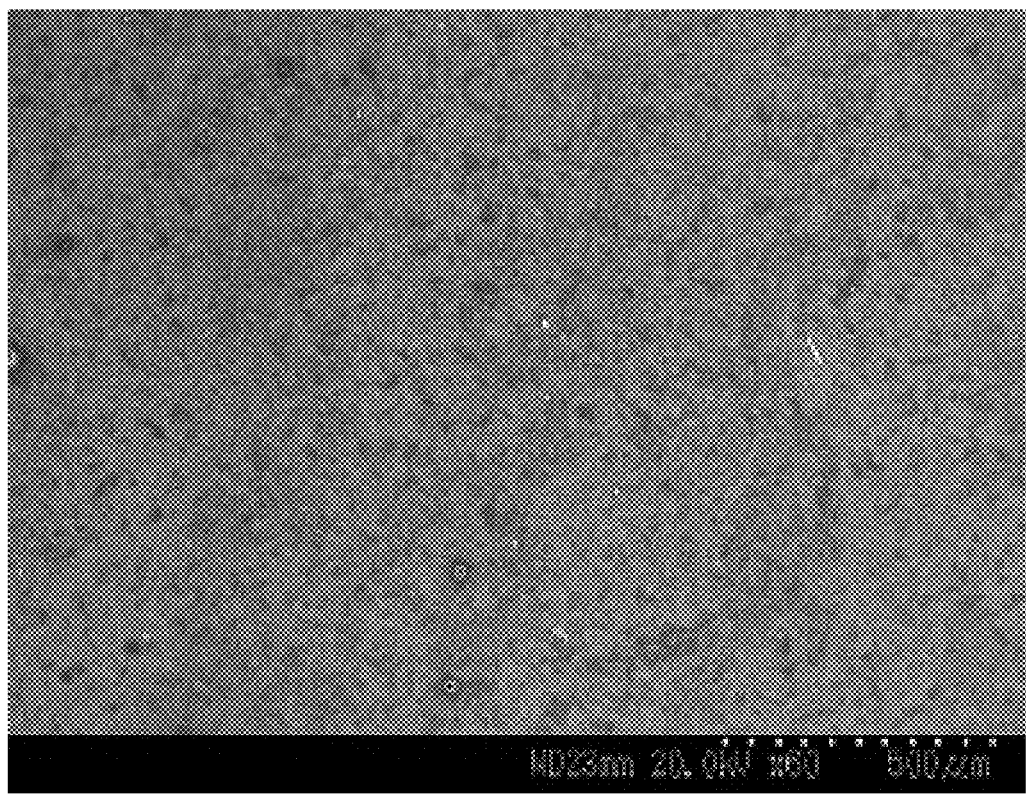
FIG. 10 is an SEM picture showing growth of continuous hydroxyapatite layer on non-hydrolyzed PLG after a 5 day mineralization.
Figure 11:
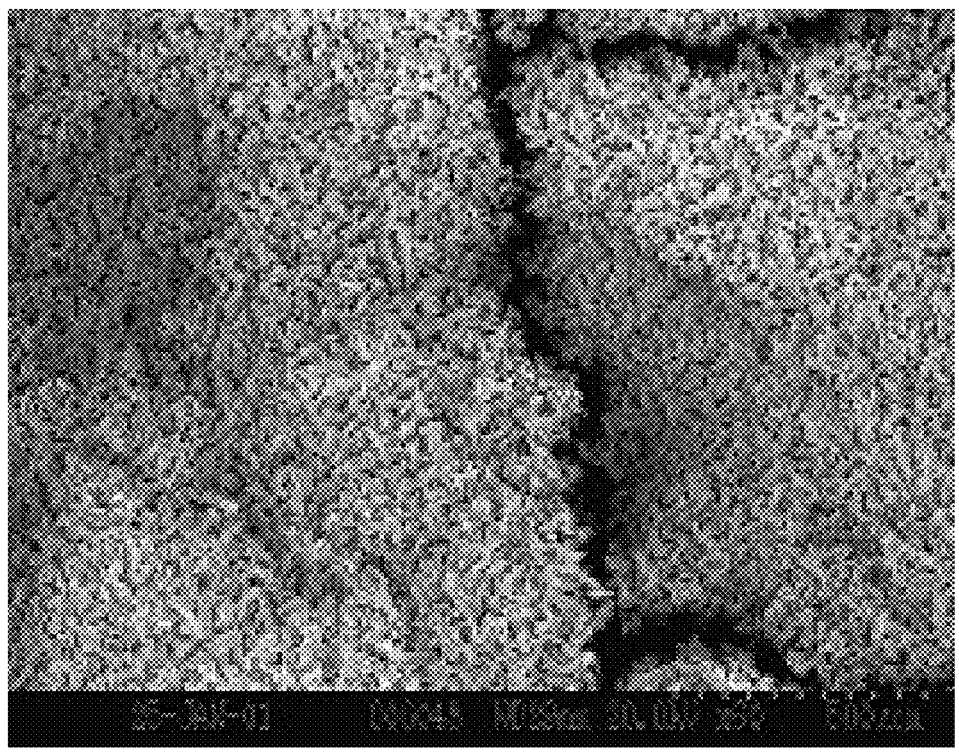
FIG. 11 is an SEM picture showing growth of continuous hydroxyapatite layer on hydrolyzed PLG after a 5 day mineralization.
Figure 12:
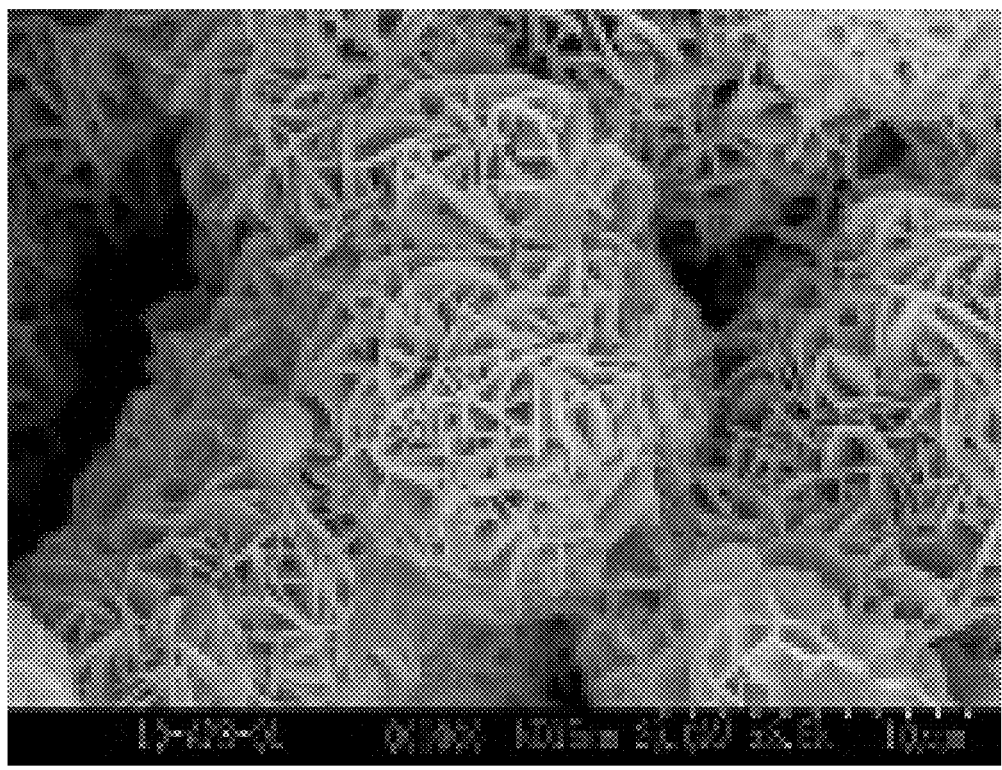
FIGS. 12 and 13 show SEM and X-ray diffraction, respectively, which demonstrate that the mineral is plate-like calcium phosphate biomineral similar in composition to bone mineral, whereby * denotes apatite peak.
Figure 13:
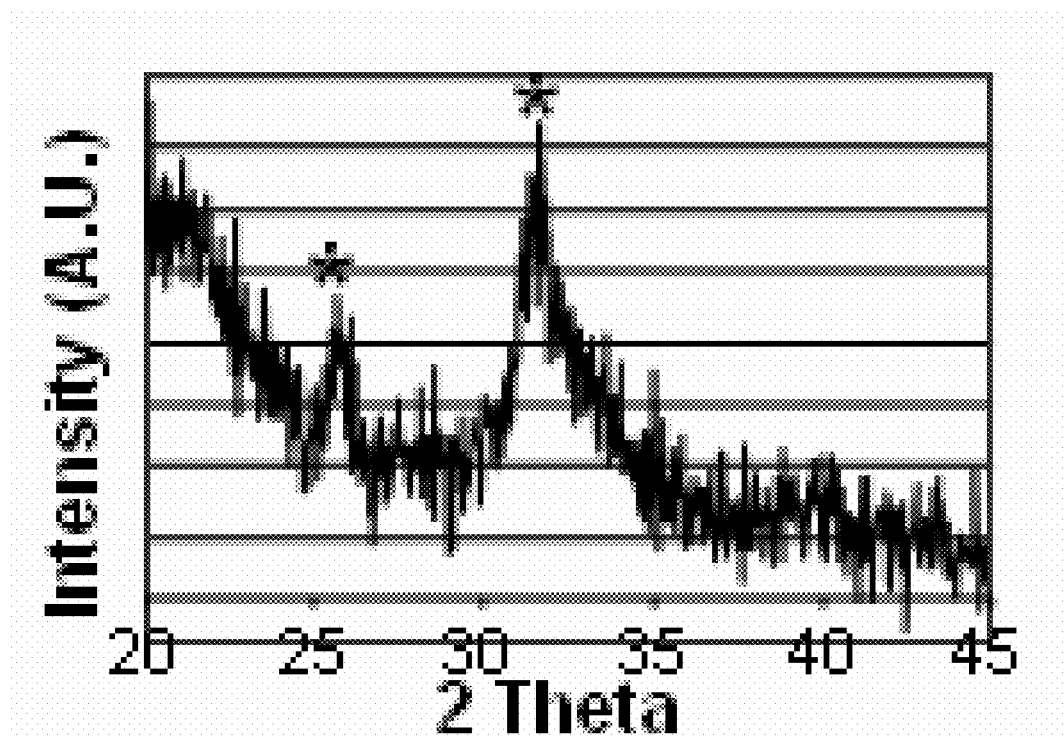
Figure 14:
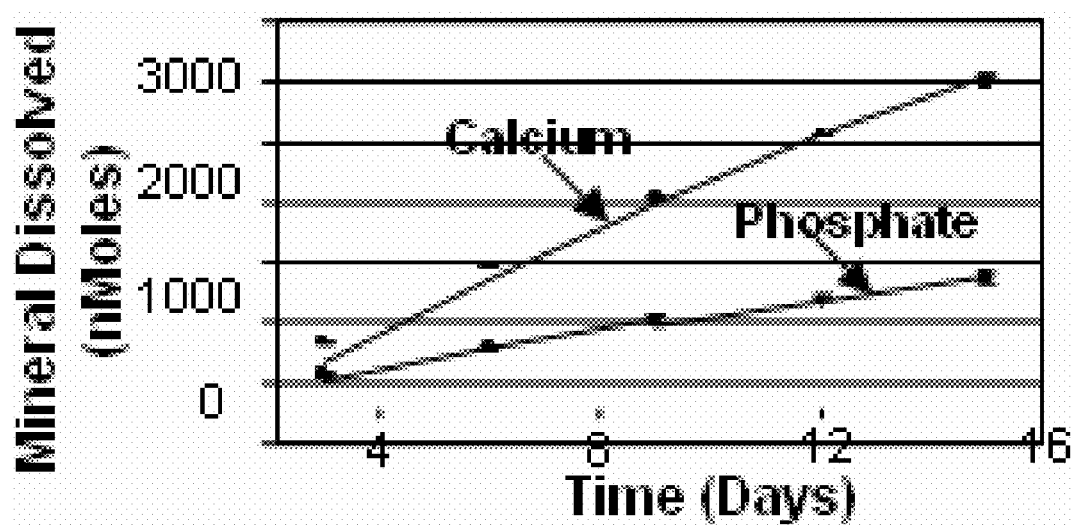
FIG. 14 is a graph demonstrating that the mineral dissolves at a controlled, constant rate over weeks in buffer, which enables constant, controlled delivery of growth factor from a calcium-phosphate coating, such as the hydroxyapatite coating.
Figure 15:
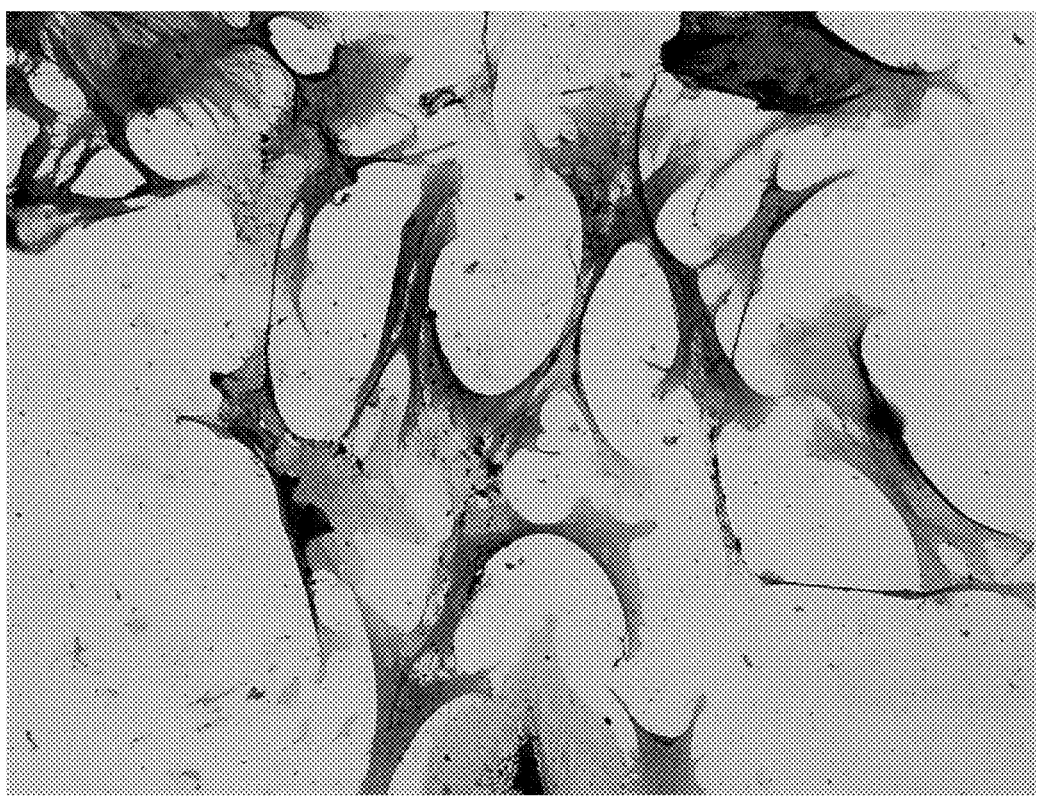
FIGS. 15 and 16 demonstrate that eBMP-2 is biologically active as evidenced by its ability to induce alkaline phosphatase upregulation (see dark staining) by mesenchymal stem cells, which is a hallmark of osteogenic differentiation.
Figure 16:
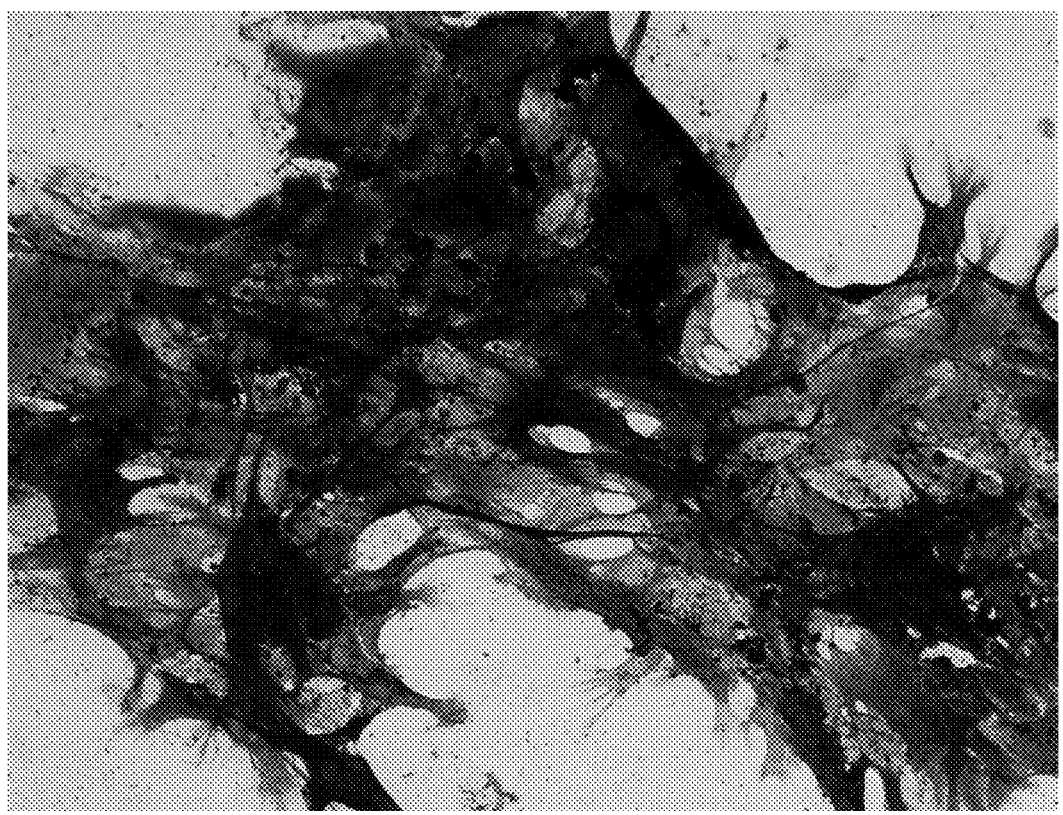
Figure 17:
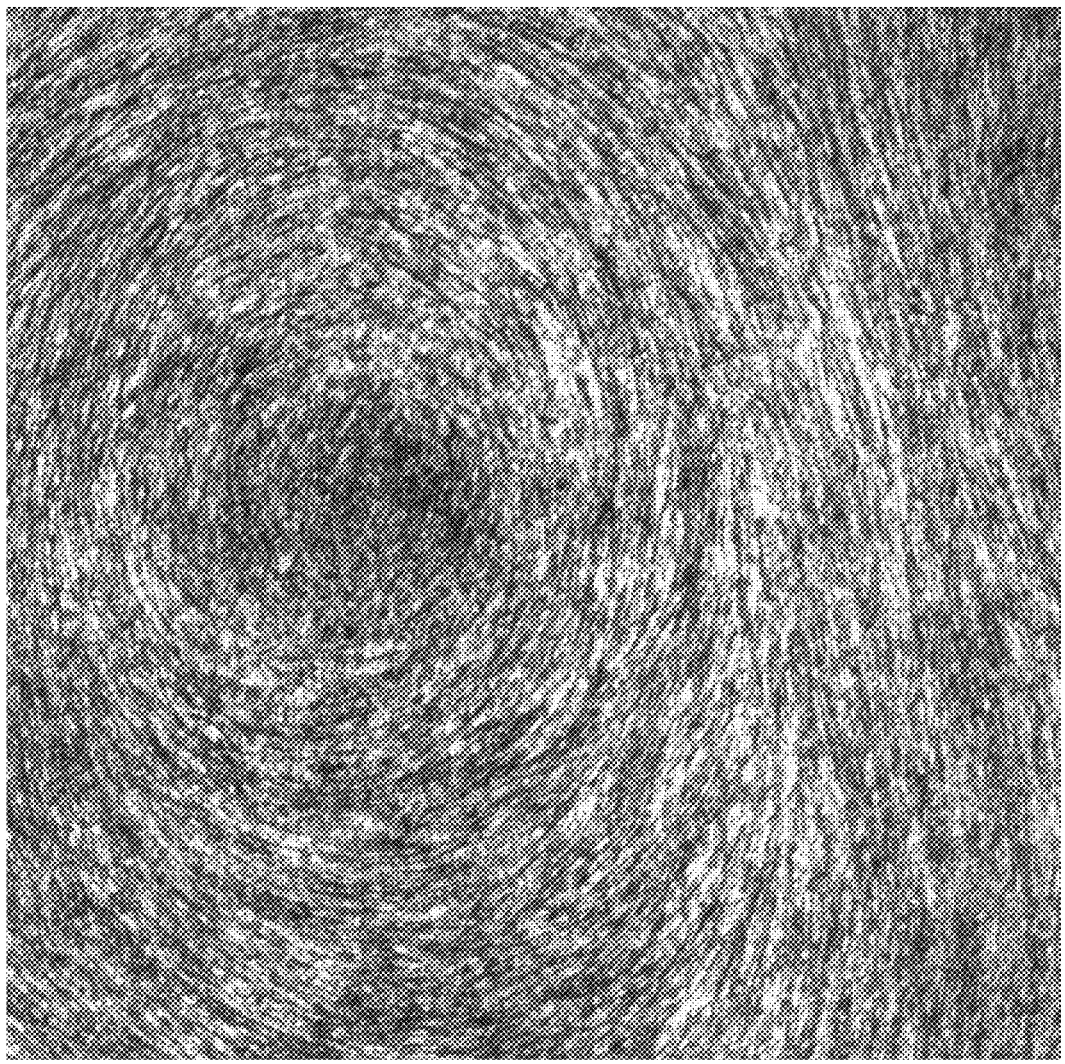
FIG. 17 shows the control substrate, whereby no calcium phosphate coating has been applied.
Figure 18:
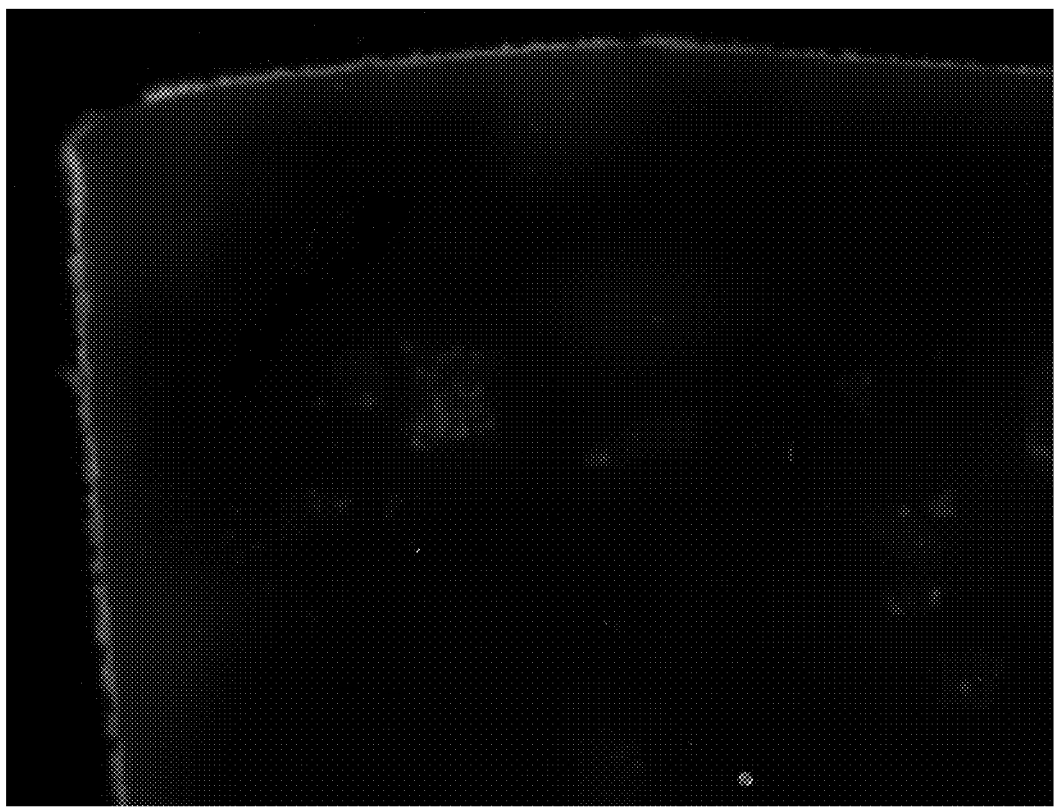
FIG. 18 shows binding of e-BMP-2 having 0 Gla (gamma carboxylated glutamic acid; Gla) within the calcium phosphate coating.
Figure 19:
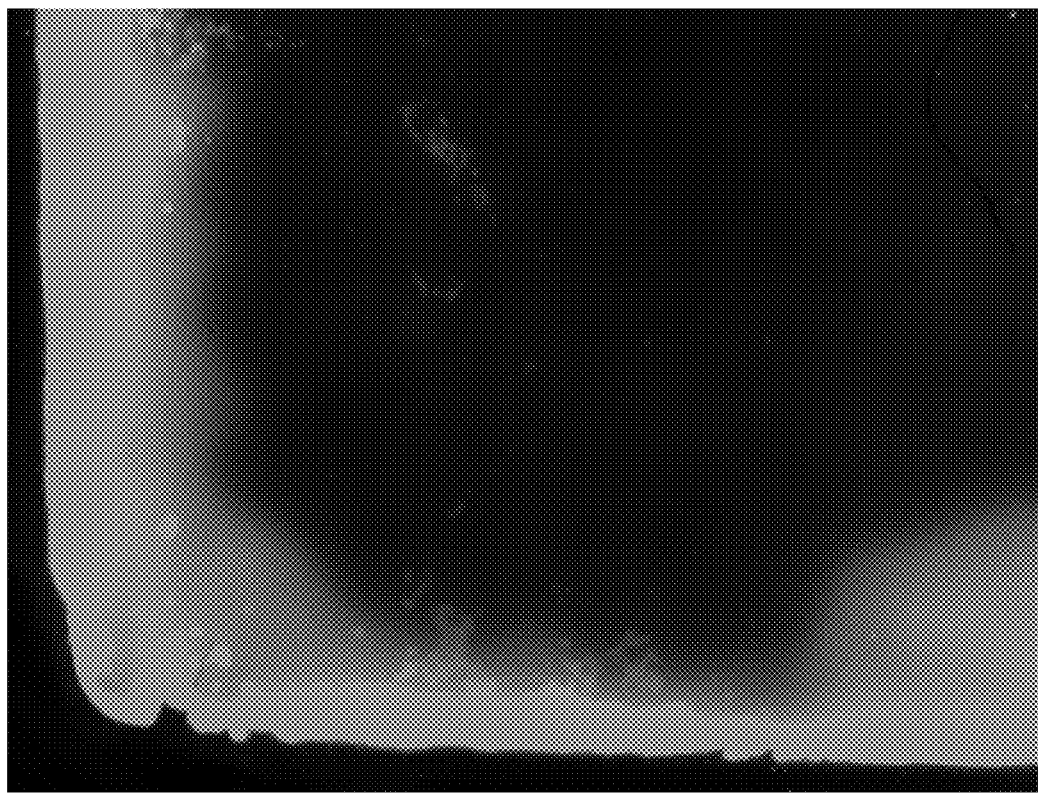
FIG. 19 shows binding of e-BMP-2 containing 1 Gla within the calcium phosphate coating.
Figure 20:
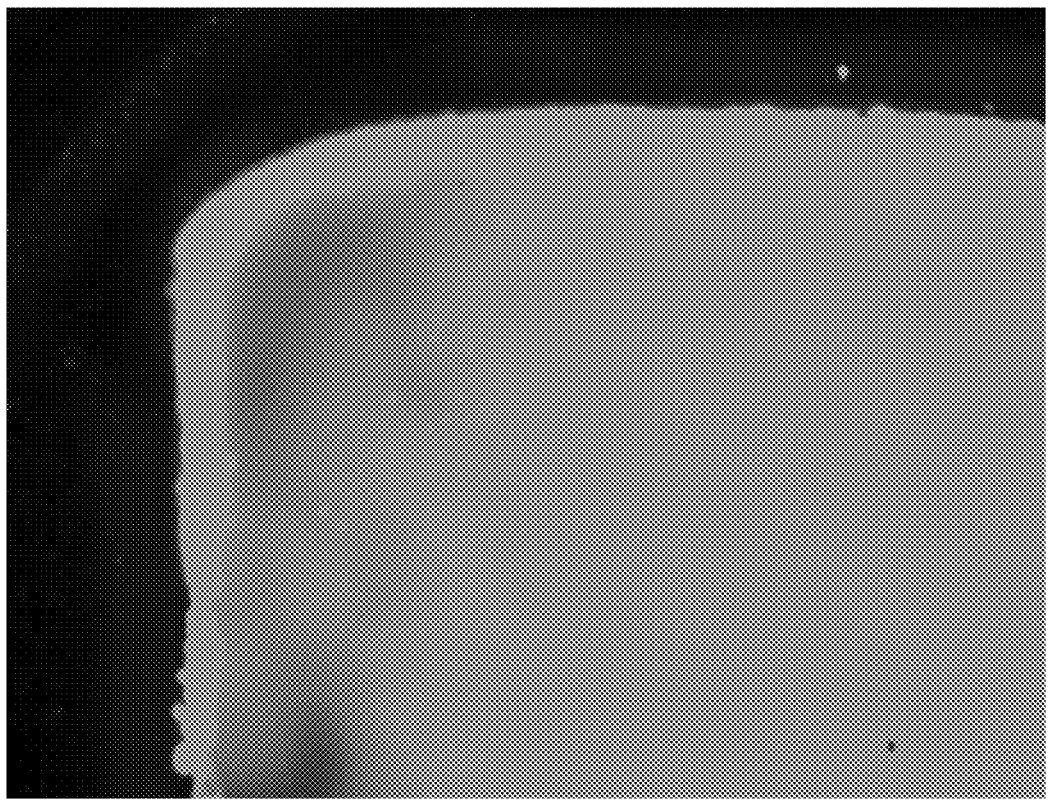
FIG. 20 shows binding of e-BMP-2 containing 2 Gla within the calcium phosphate coating.
Figure 21:
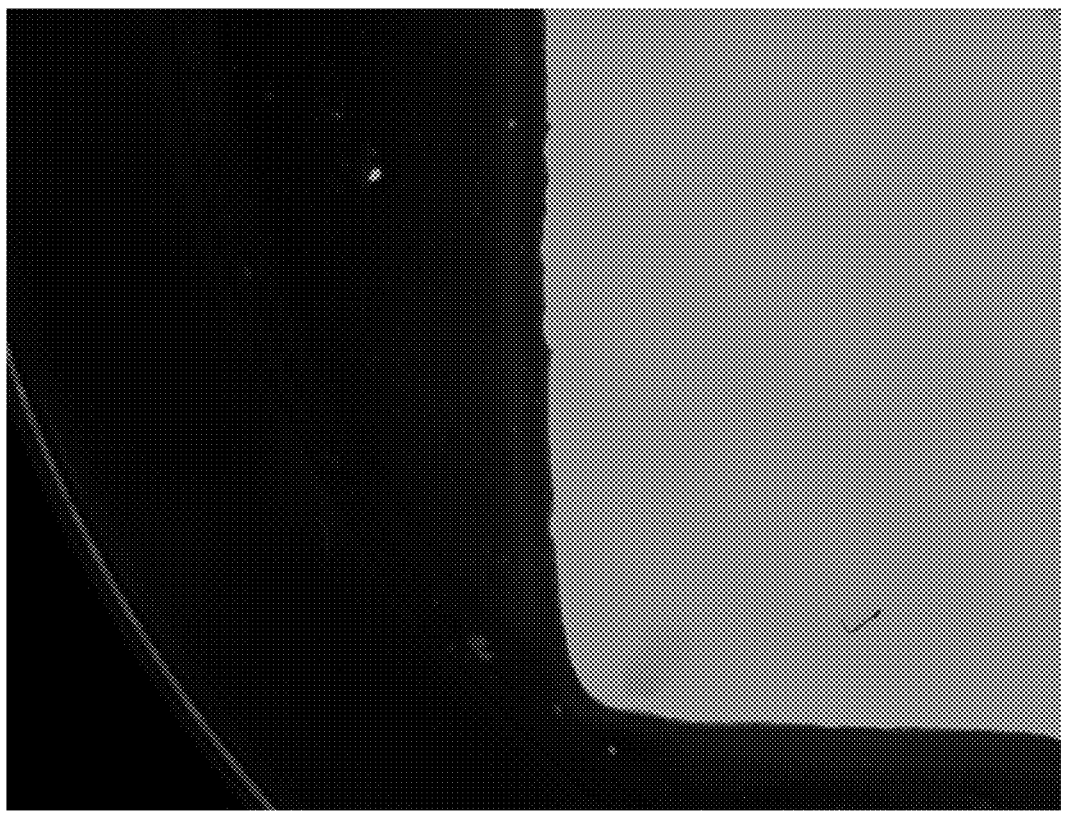
FIG. 21 shows binding of e-BMP-2 having 3 Gla within the calcium phosphate coating.
Figure 22:
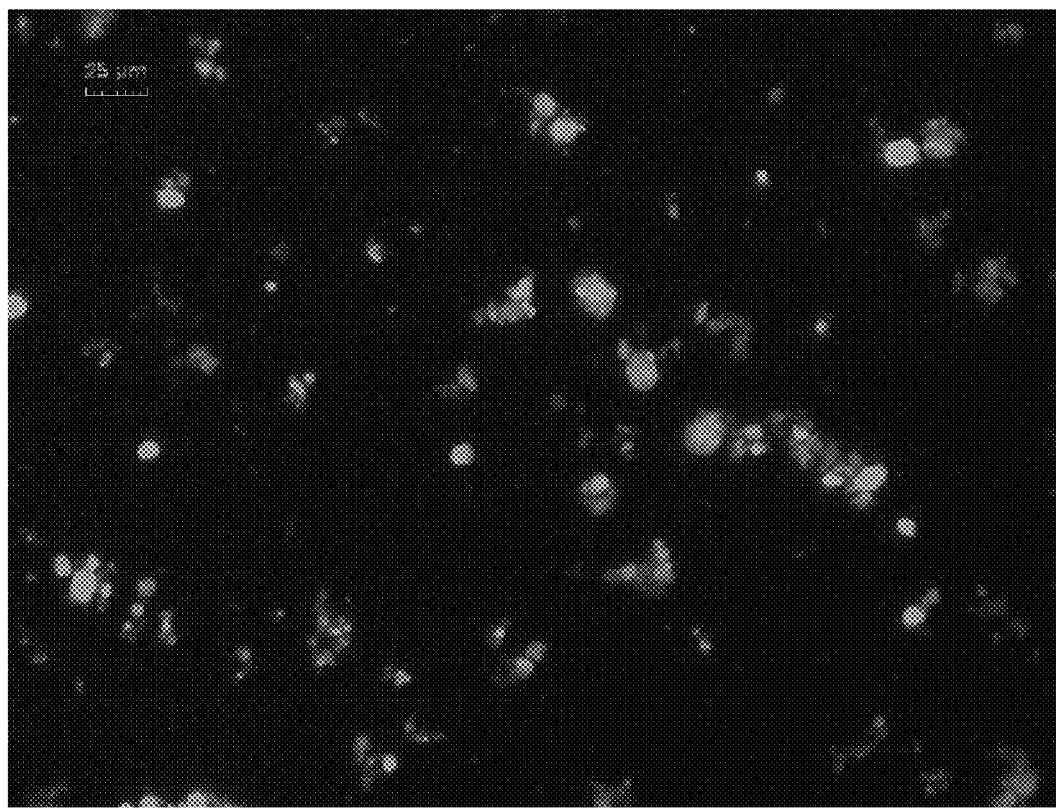
FIG. 22 shows binding of e-BMP-2 having therein SEQ ID NO: 17 within the calcium phosphate coating.
Figure 23:
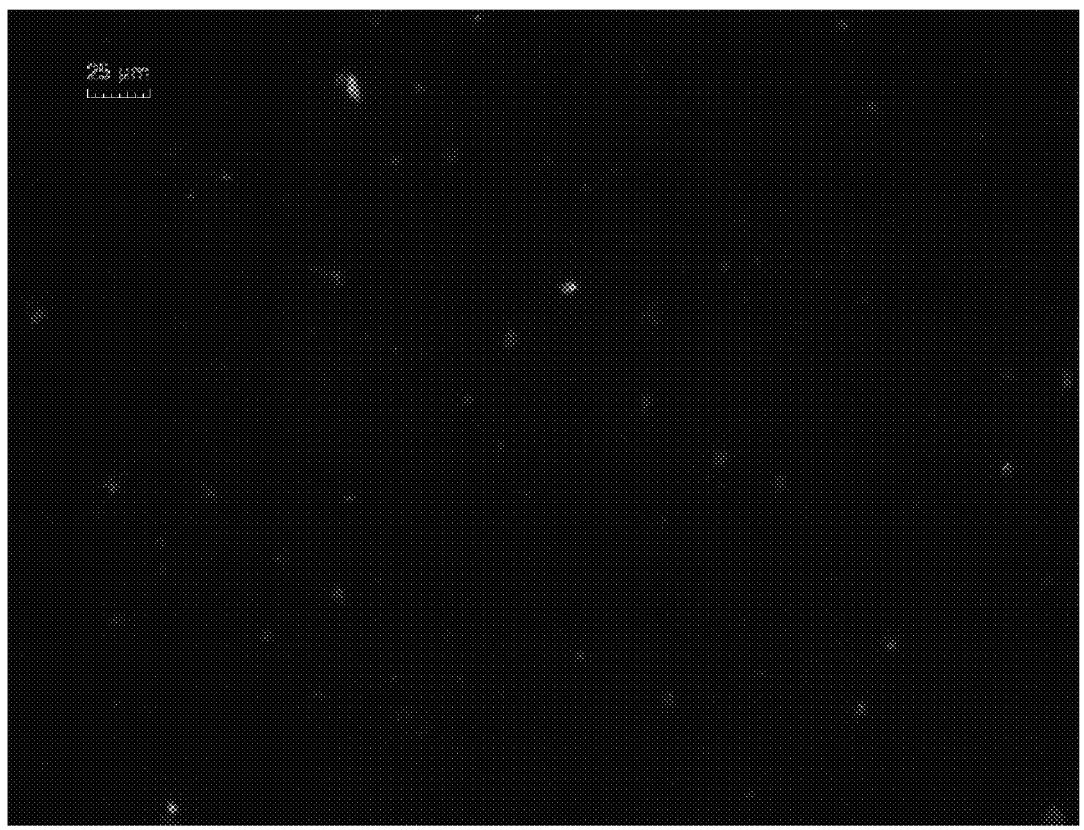
FIG. 23 shows binding of e-BMP-2 having therein SEQ ID NO: 18 within the calcium phosphate coating.
Figure 24:
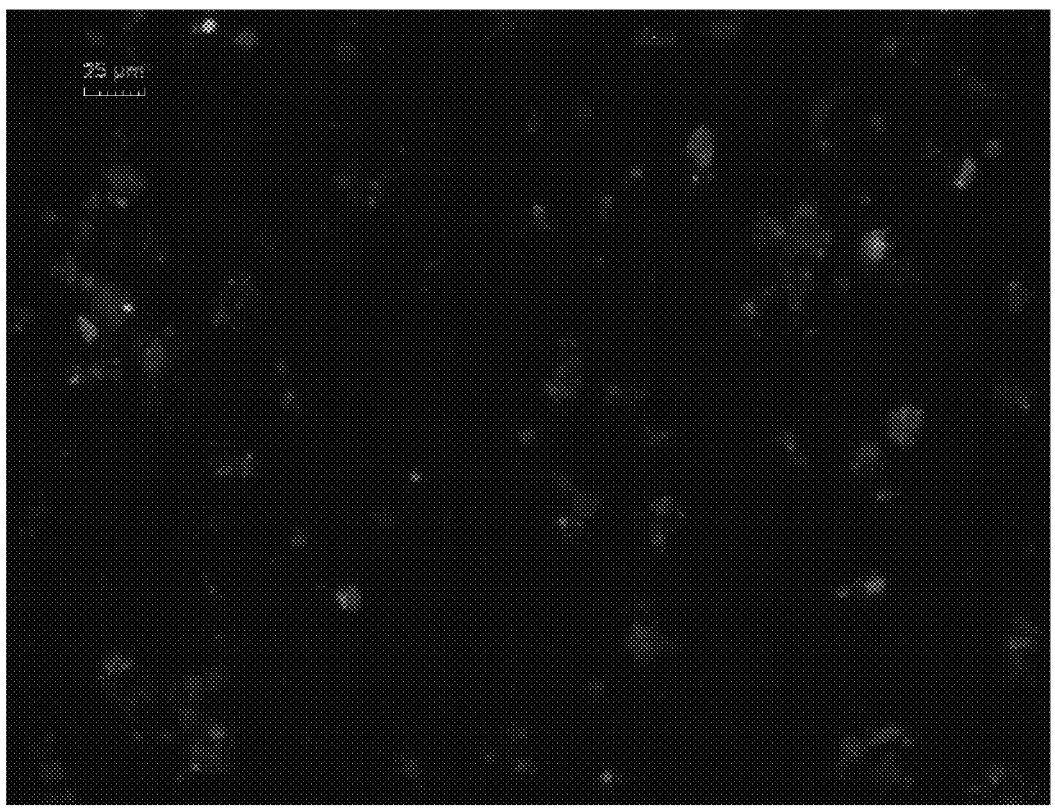
FIG. 24 shows binding of e-BMP-2 having therein SEQ ID NO: 19 within the calcium phosphate coating.
Figure 25:
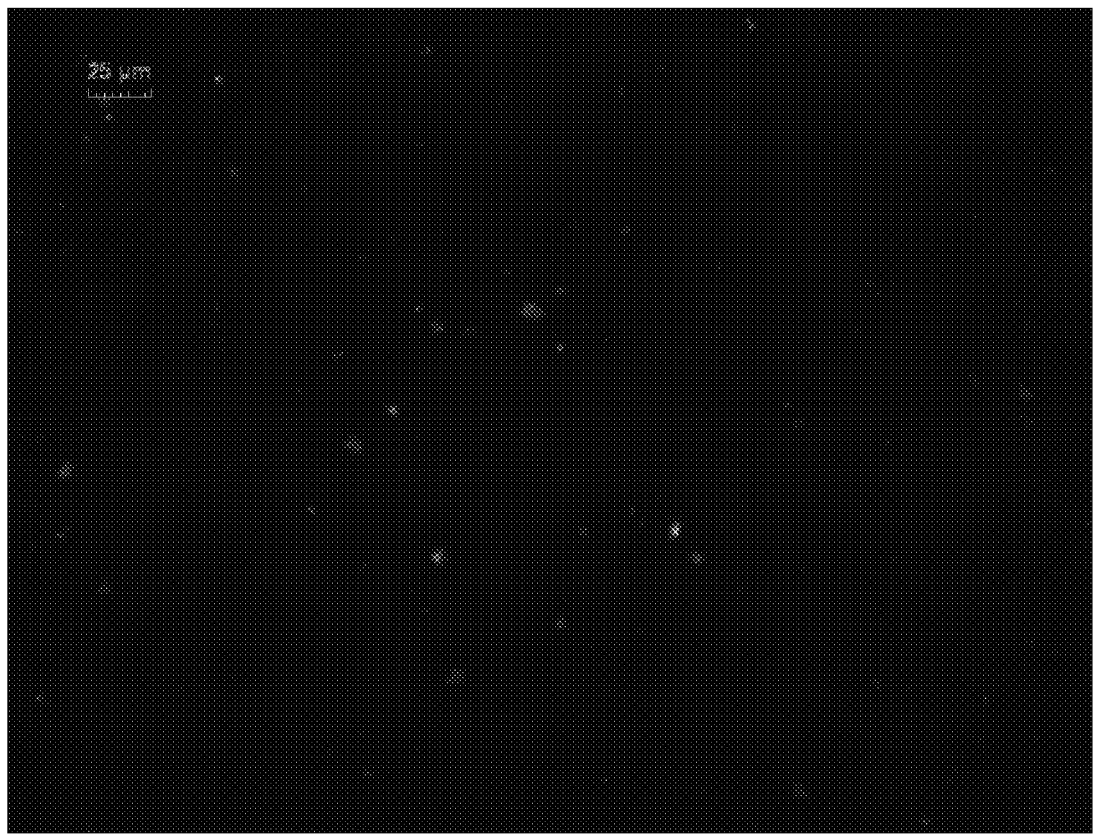
FIG. 25 shows binding of e-BMP-2 having therein SEQ ID NO: 14 within the calcium phosphate coating.
Figure 26:
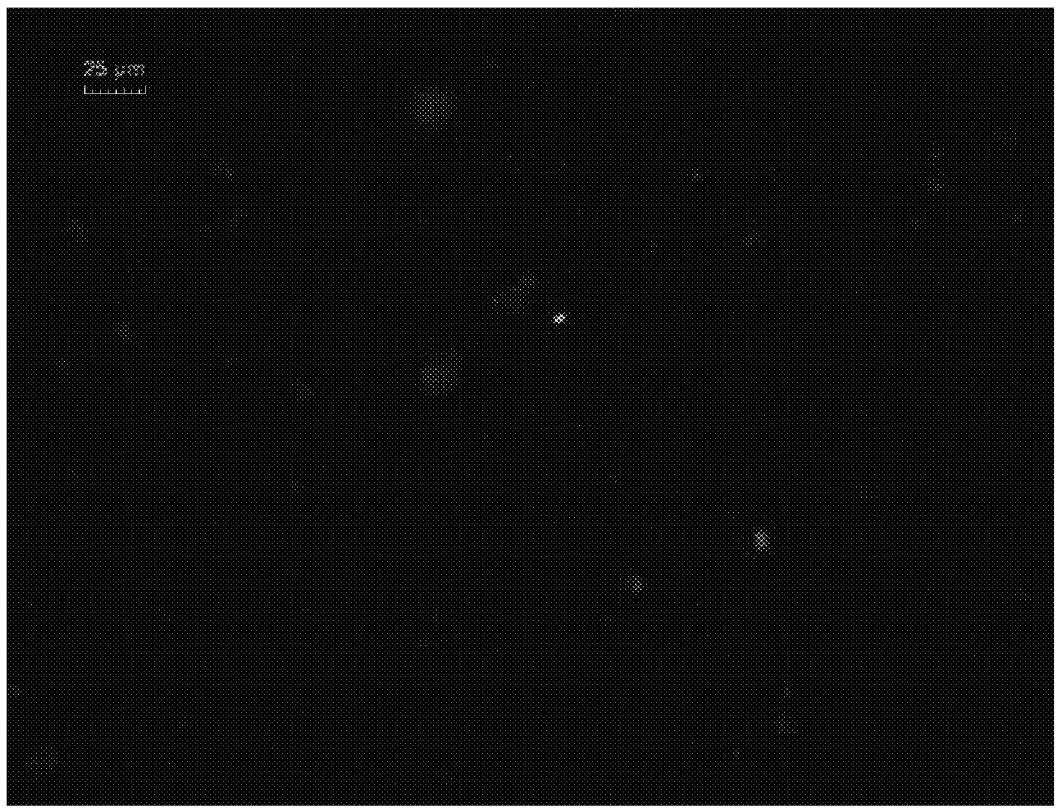
FIG. 26 shows binding of e-BMP-2 having therein SEQ ID NO: 15 within the calcium phosphate coating.
Figure 27:
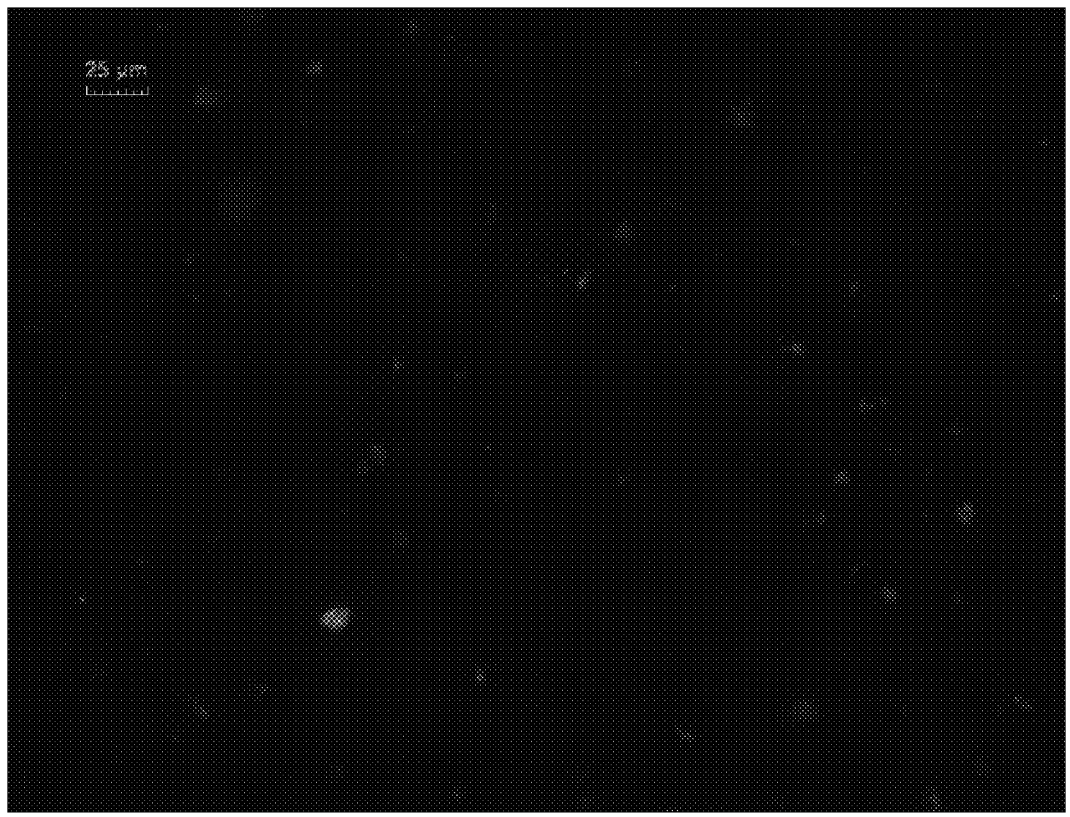
FIG. 27 shows binding of e-BMP-2 having therein SEQ ID NO: 16 within the calcium phosphate coating.
Figure 28:
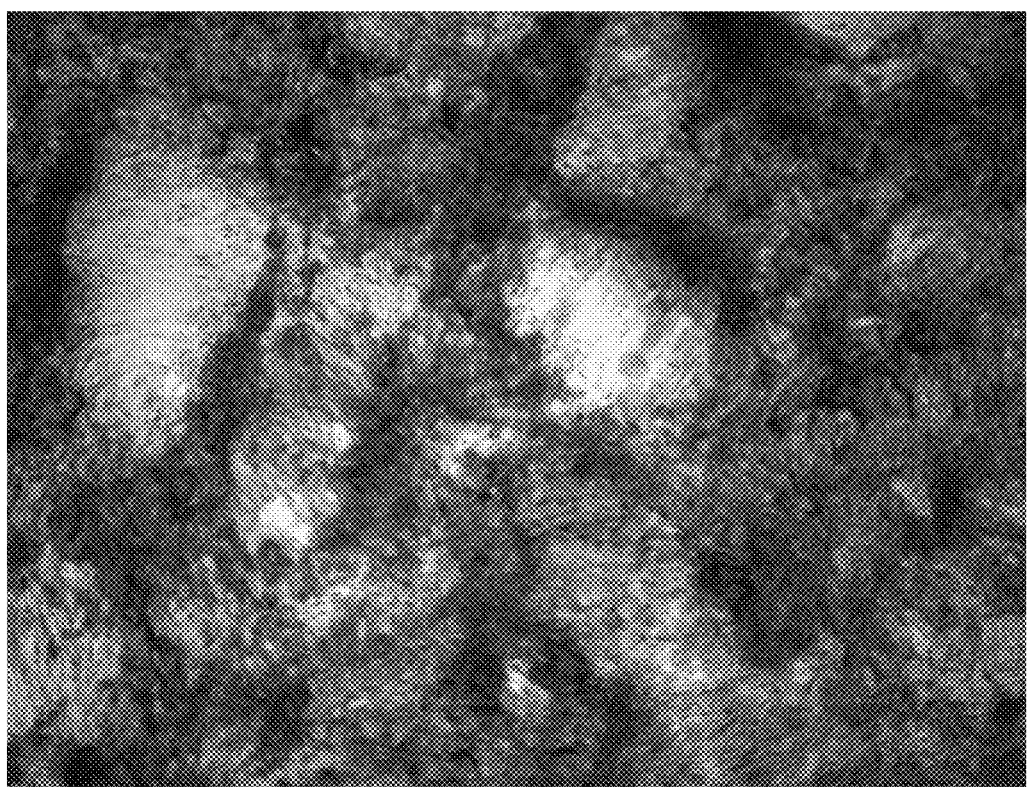
FIG. 28 shows Alizarin Red S (ARS) staining image of rhBMP-2 (recombinant human BMP-2) as the control.
Figure 29:
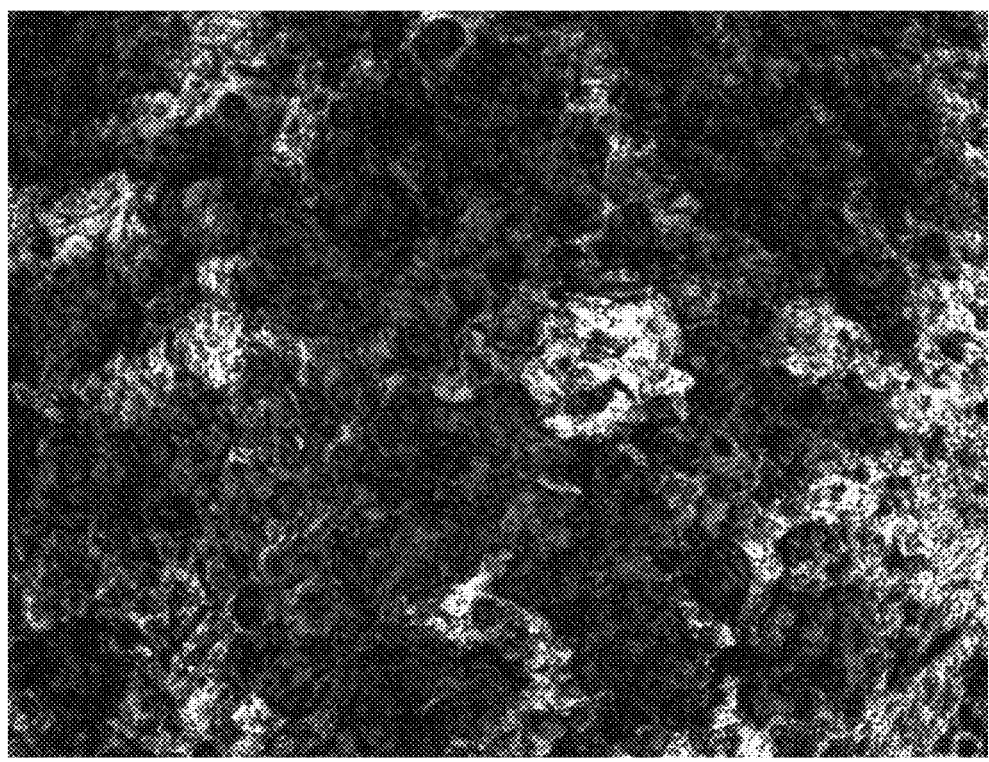
FIG. 29 shows Alizarin Red S (ARS) staining image of e-BMP-2 having therein SEQ ID NO: 20.
Figure 30:
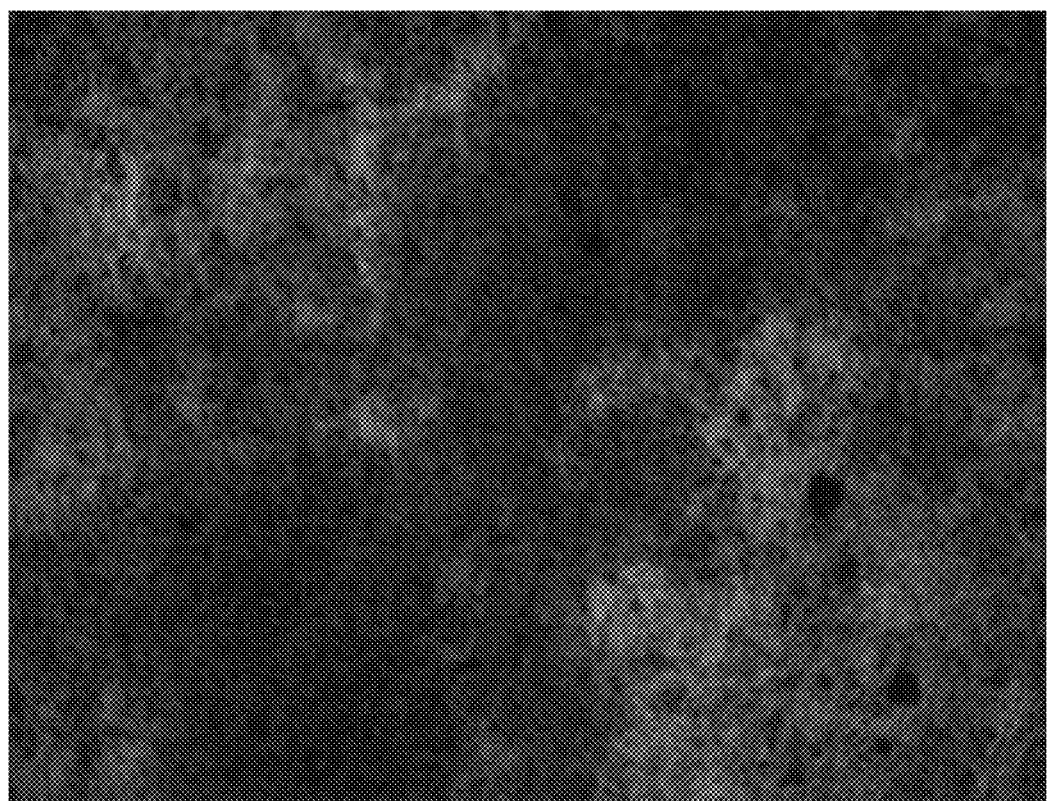
FIG. 30 shows Alizarin Red S (ARS) staining image of e-BMP-2 having therein SEQ ID NO: 17.
Figure 31:
FIG. 31 shows Alizarin Red S (ARS) staining image of e-BMP-2 having therein SEQ ID NO: 18.
Figure 32:
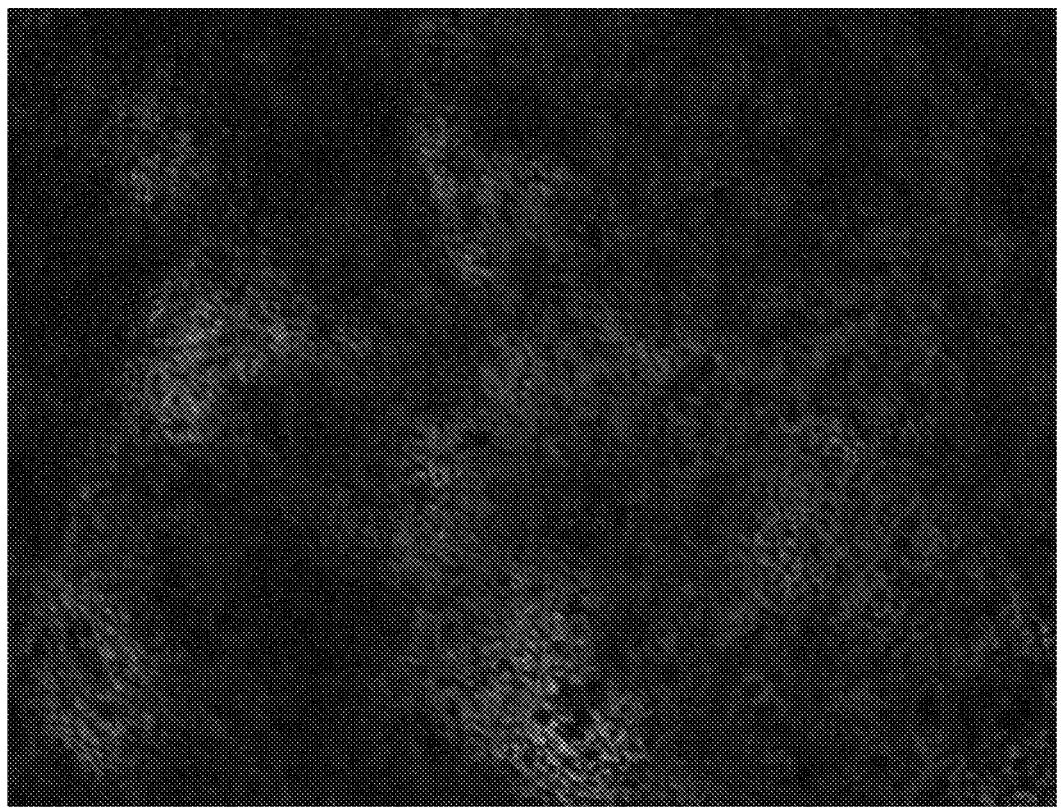
FIG. 32 shows Alizarin Red S (ARS) staining image of e-BMP-2 having therein SEQ ID NO: 19.
Figure 33:
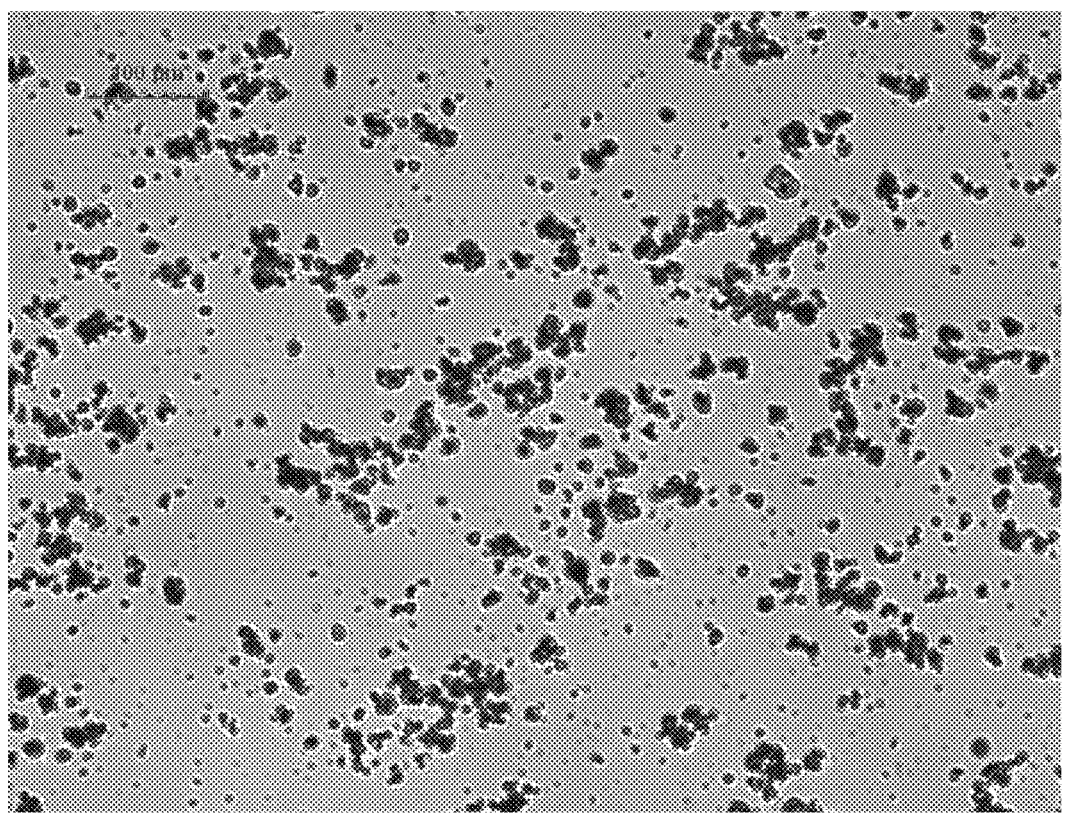
FIG. 33 shows brightfield image of hydroxyapatite particles suspended in phosphate buffered saline.
Figure 34:
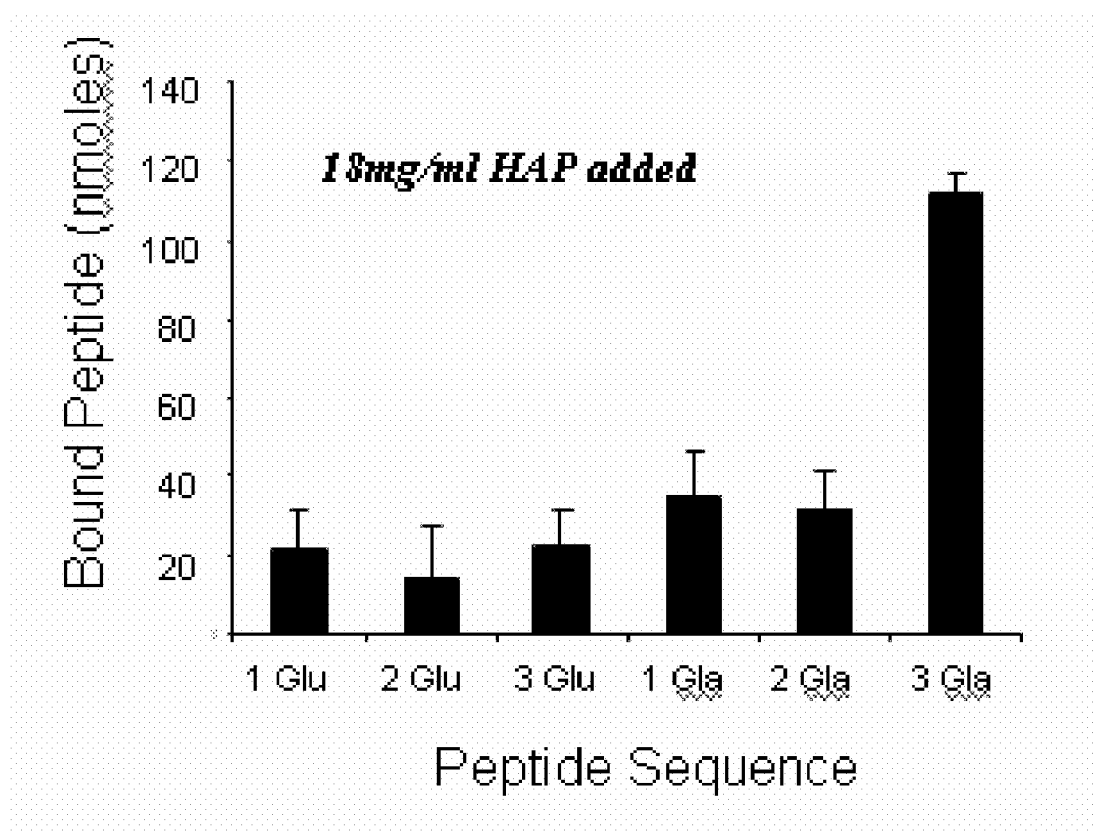
FIG. 34 is a graph illustrating differences in bound peptides vs. the number of Glu and Gla residues in the peptide in a solution of 18 mg/ml of hydroxyapatite (HAP) respecting the images showing binding of fluorescein-labeled particles shown in FIGS. 22-27.
Figure 35:
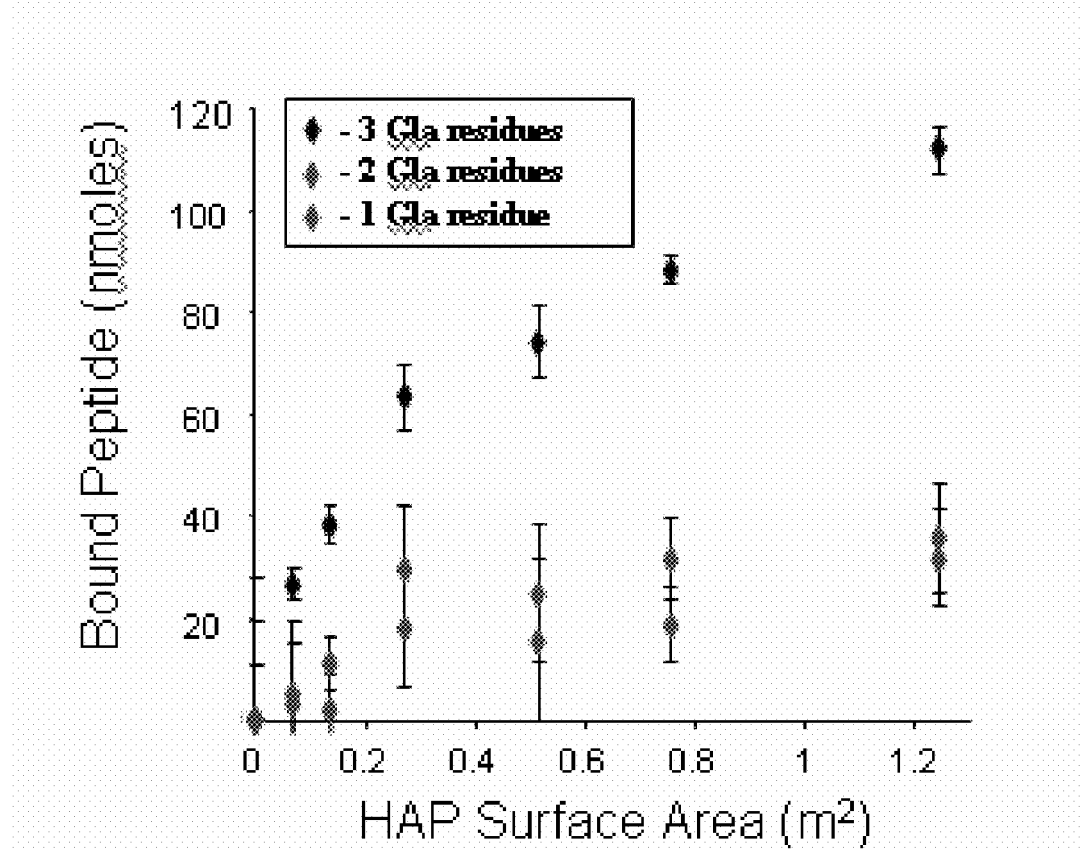
FIG. 35 is a graph illustrating the bound peptides vs. the surface area of the hydroxyapatite for various e-BMP-2 having therein SEQ ID NO: 17, SEQ ID NO: 18 and SEQ ID NO: 19 respecting the images showing binding of fluorescein-labeled peptides shown in FIGS. 22-27.
Figure 36:
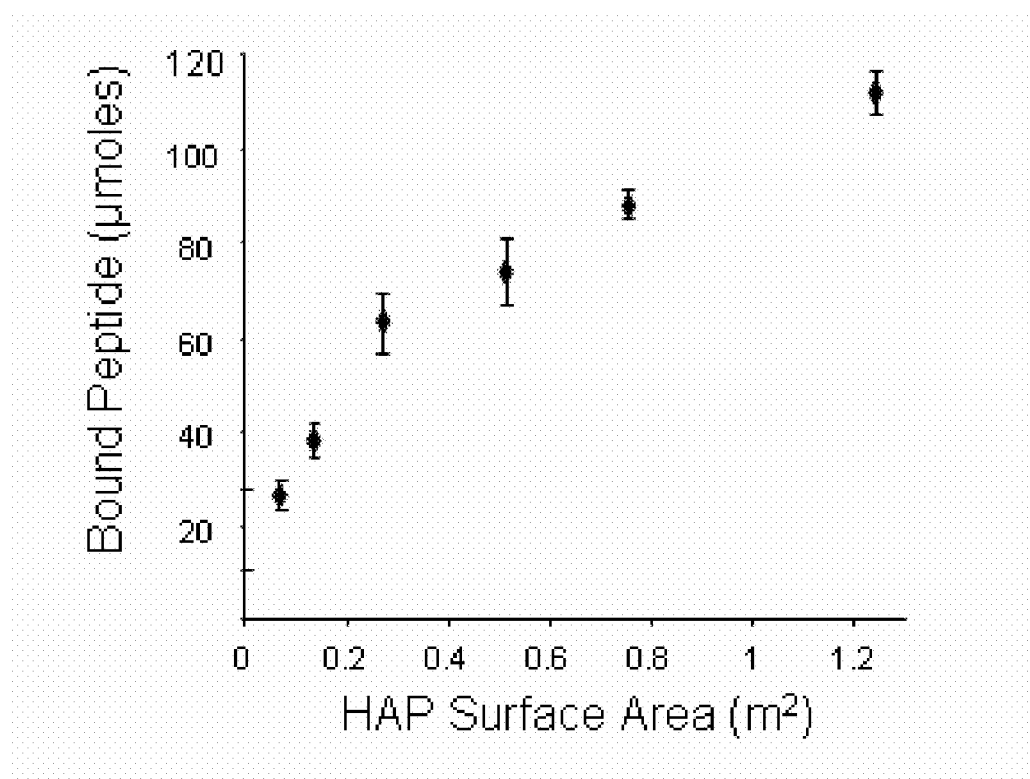
FIG. 36 is a graph illustrating the bound peptides vs. the surface area of the hydroxyapatite coating, whereby the concentration was 0.111 μmol engineered peptide/18 mg HAP.
Figure 37:
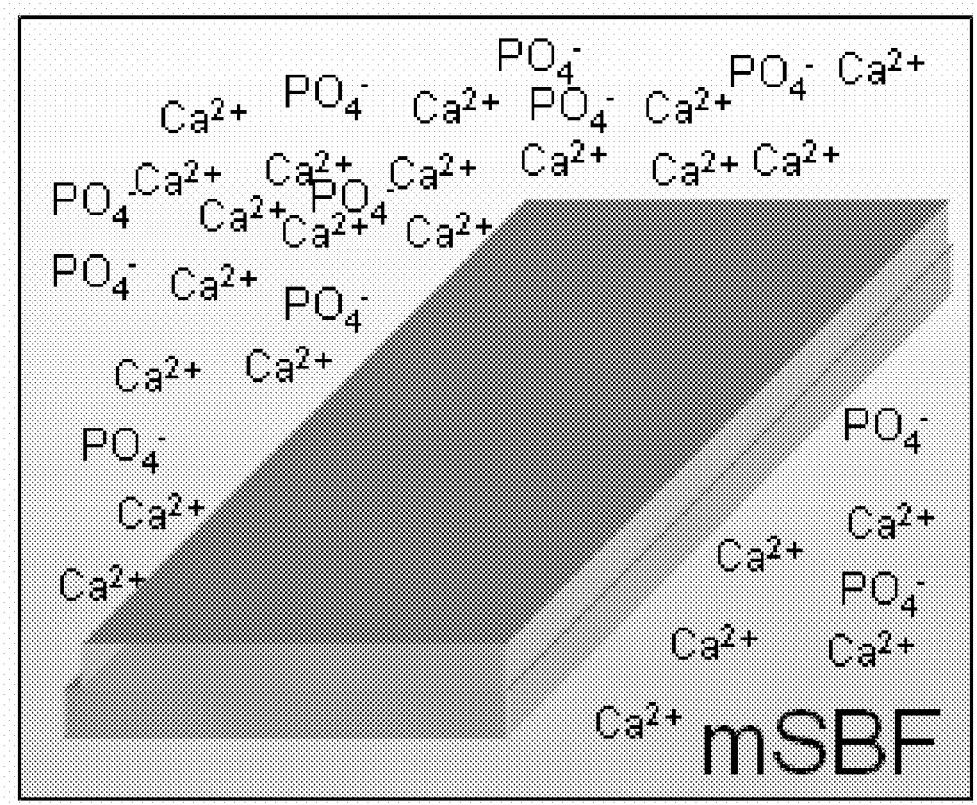
FIG. 37 shows a calcium phosphate coating on a poly(α-hydroxy ester) film, whereby the surrounding solution contains calcium and phosphate ions.
Figure 38:
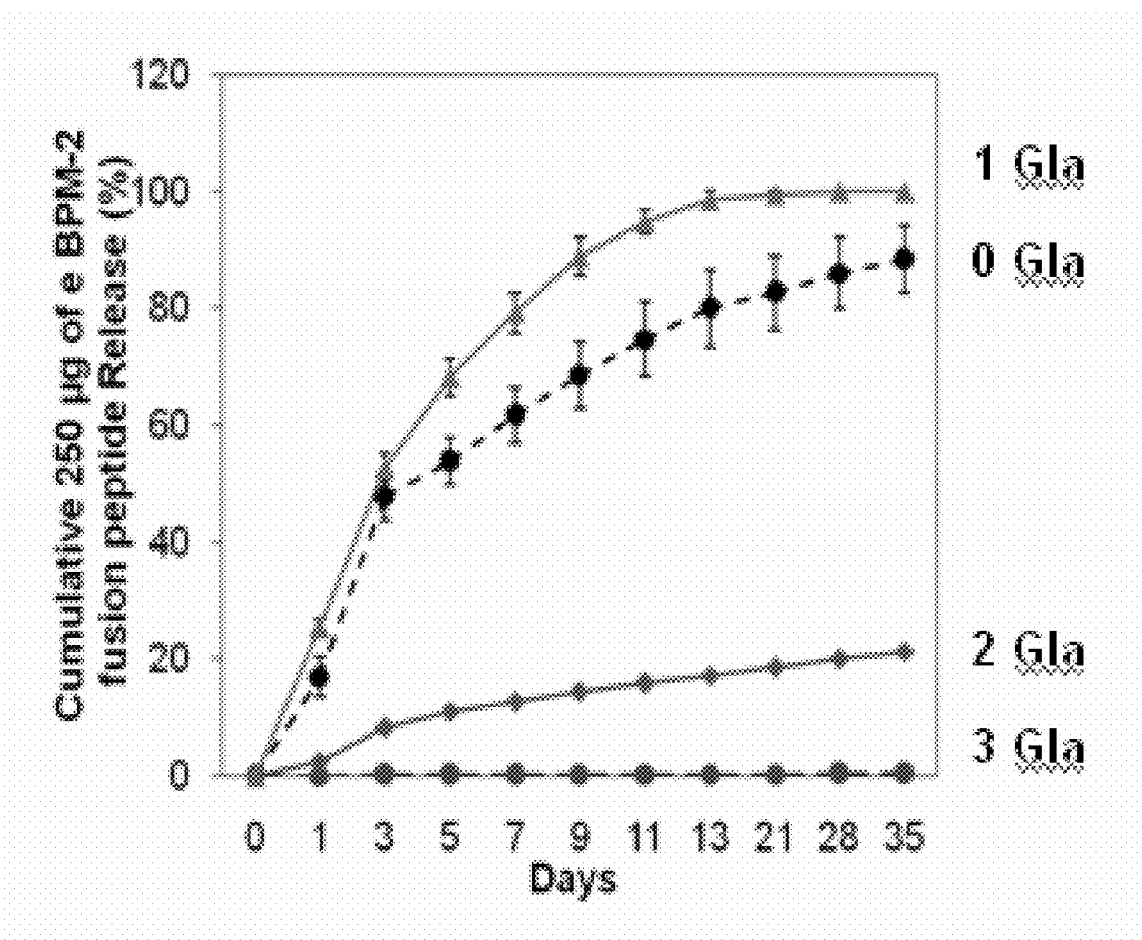
FIG. 38 is a graph illustrating cumulative release of various e-BMP-2 having therein 0 Gla residues, SEQ ID NO: 17, SEQ ID NO: 18, SEQ ID NO: 19 and SEQ ID NO: 20 respecting the fluorescence images shown in FIGS. 18-21.
Figure 39:
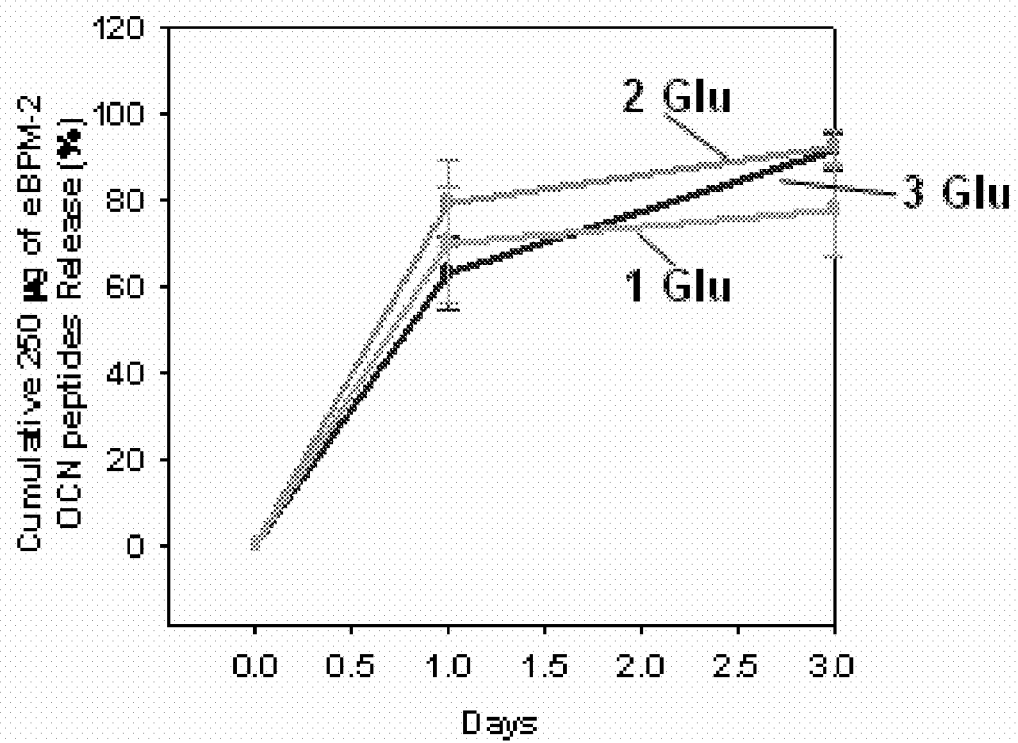
FIG. 39 is a graph illustrating cumulative release of various e-BMP-2 having therein SEQ ID NO: 14, SEQ ID NO: 15 and SEQ ID NO: 16 from hydroxyapatite respecting the shown in FIGS. 18-21.
Figure 40:
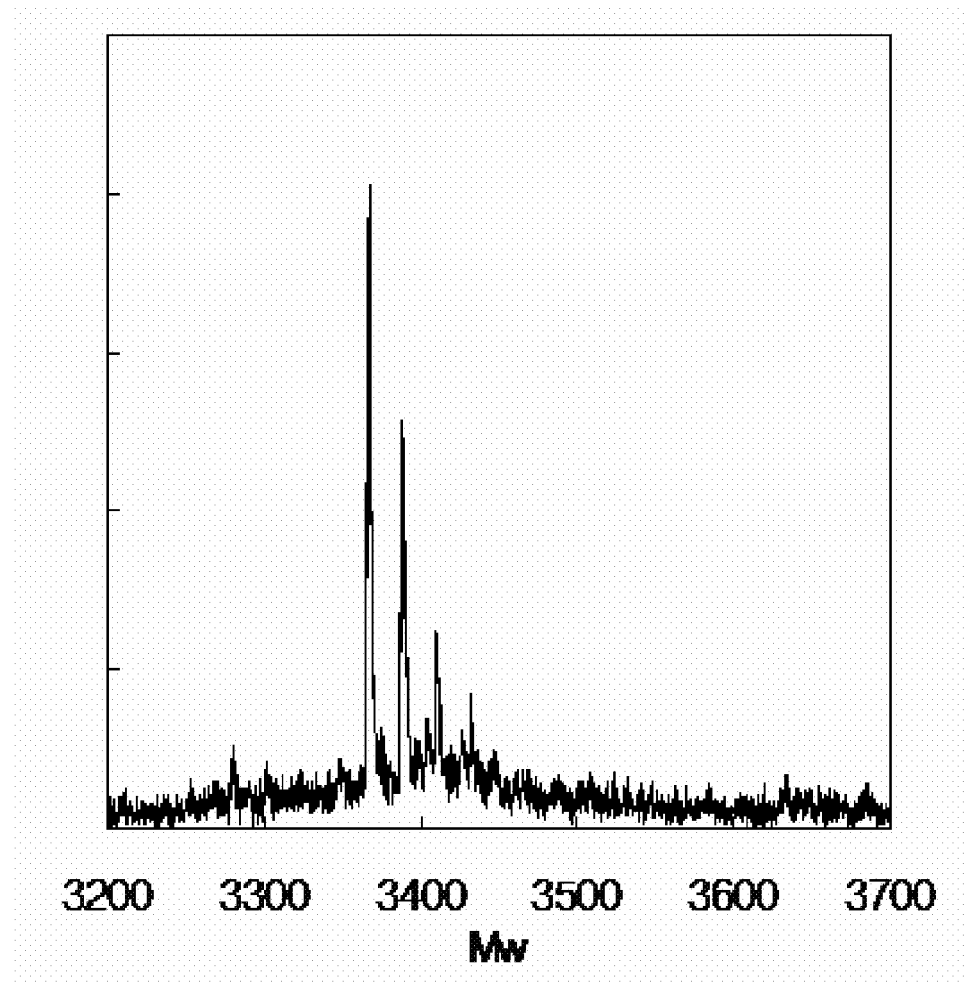
FIG. 40 is a MALDI-mass spectrometry of an e-BMP-2 having therein SEQ ID NO: 19 (also referred to as γGla-OCN-1).
Figure 41:
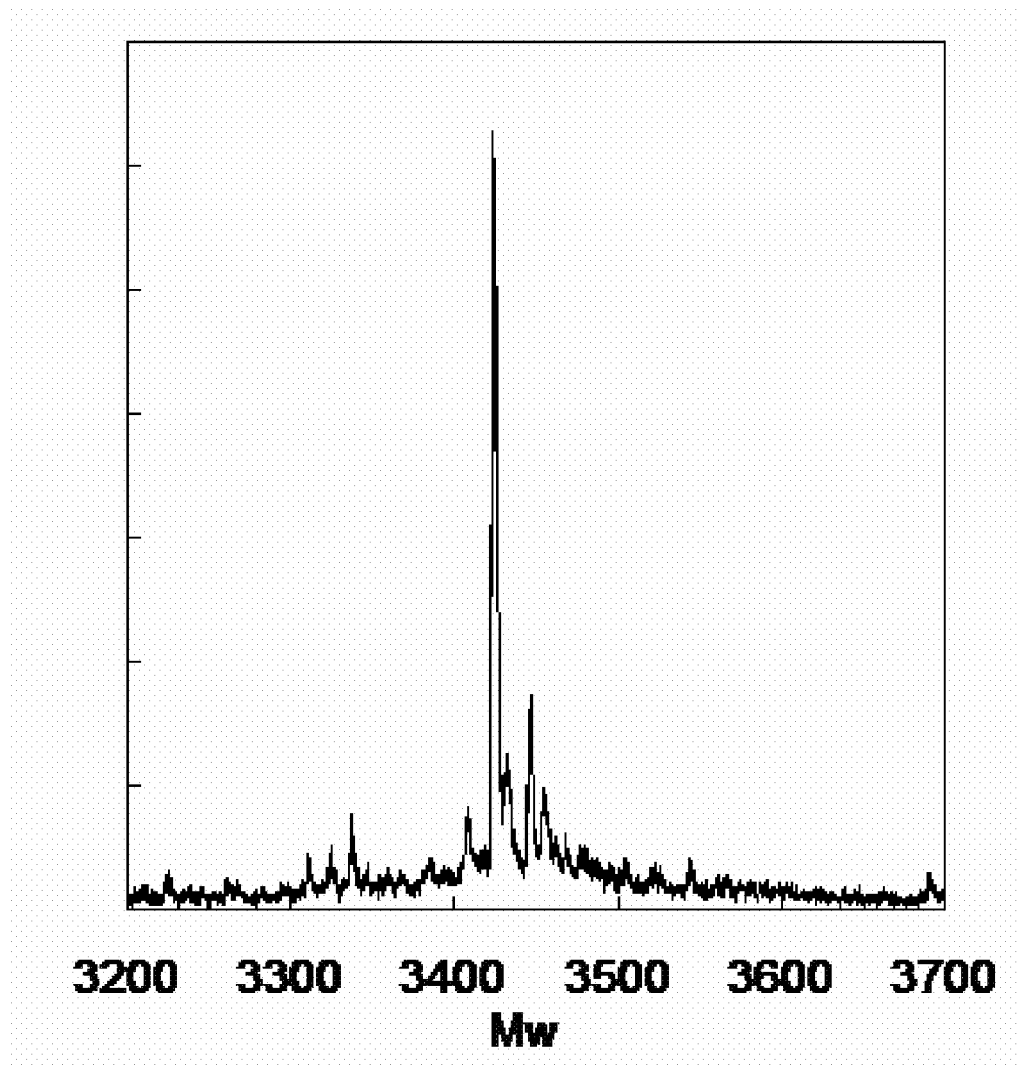
FIG. 41 is a MALDI-mass spectrometry of an e-BMP-2 having therein SEQ ID NO: 18 (also referred to as γGla-OCN-2).
Figure 42:
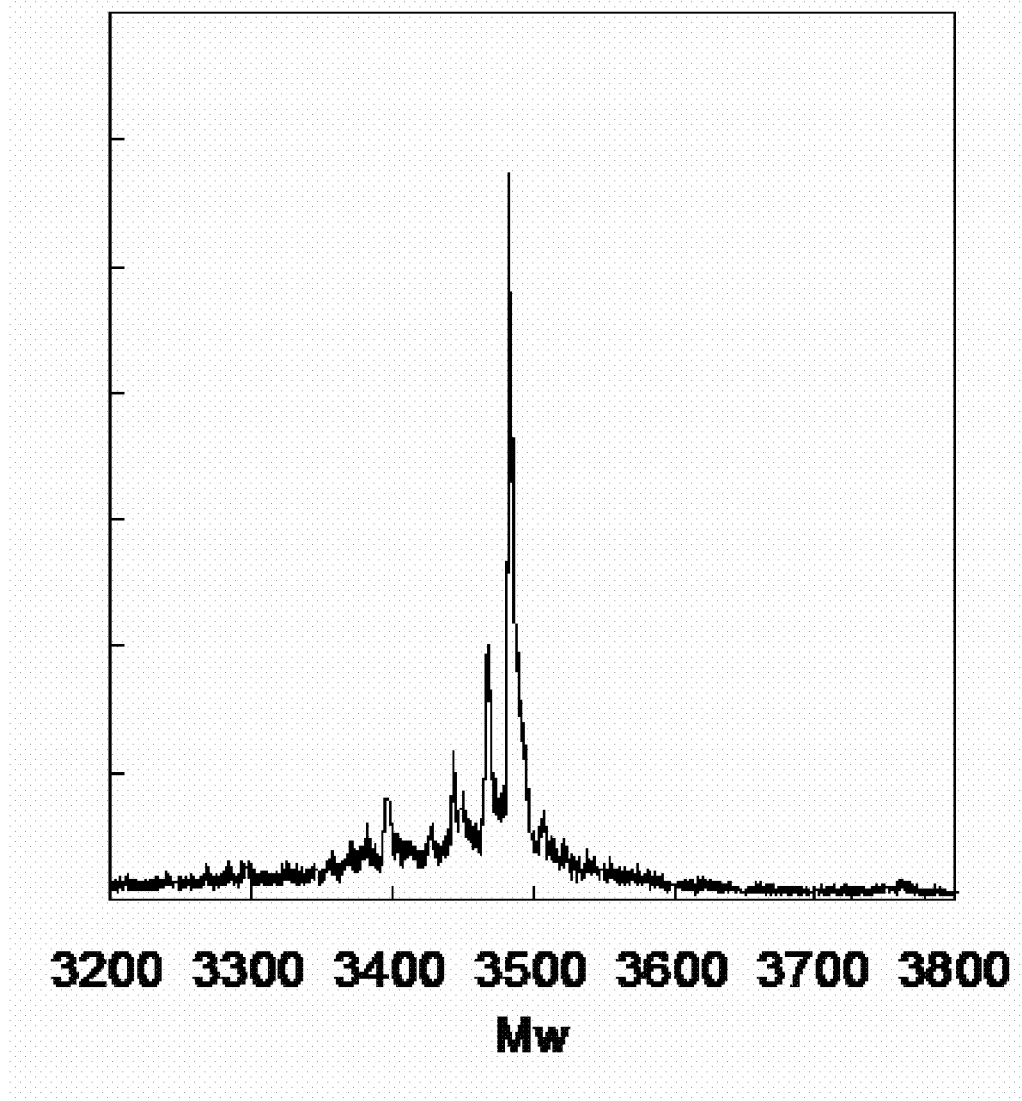
FIG. 42 is a MALDI-mass spectrometry of an e-BMP-2 having therein SEQ ID NO: 17 (also referred to as γGla-OCN-3).

Binding growth factors to calcium phosphate minerals. Characterization of binding of engineered bone morphogenetic protein-2 peptide (eBMP-2) to CaP mineral materials is characterized. Preliminary results demonstrate that eBMP-2 forms strong ionic bonds to hydroxyapatite in solution. (See, FIGS. 10 and 11). Ionic binding advantageously provides suitable controlled delivery of growth factor through dissolution of the CaP layer. e-BMP-2 also promotes osteogenic differentiation. (See, FIGS. 12 and 13). Native BMP-2 will be used because it has a high intrinsic affinity for CaP minerals.

Without being bound to any specific theory, it is hypothesized that ionic binding is achieved between $Ca^{2+}$ in the CaP material and mineral binding fragments in the growth factor, whereby the binding fragments include at least about eight consecutive glutamic acid residues, e.g., EEEEEEEE or at least about eight consecutive aspartic acid residues, e.g., DDDDDDDD. (Harris H, et al., "Functional analysis of bone sialoprotein: identification of the hydroxyapatite-nucleating and cell-binding domains by recombinant peptide expression and site-directed mutagenesis," *Bone* 2000, 27:795-802; and Tye C, et al., "Delineation of the hydroxyapatite-nucleating domains of bone sialoprotein," *J. Biol. Chem.* 2003, 278: 7949-7955.)

EXAMPLE 5

Incorporation of growth factors into CaP coatings on resorbable bone screws. Controlled incorporation and release of BMP-2 to/from CaP coatings. To characterize incorporation of BMP-2 into CaP mineral coatings, 1-labeled BMP-2 from ICN Biomedicals will be used. Radio-labeling is a highly sensitive method for characterizing protein incorporation and release. Mineral coatings will be grown on PLLA as described herein in solutions containing 10-1000 nM BMP-2 with 10 nM I-labeled BMP-2 used as a tracer. The CaP coating will bind BMP-2 with 50-100% efficiency in the soluble BMP-2 concentration range.

The scaffolds will be removed from solution, rinsed with PBS, and analyzed for radioactivity using a scintillation counter. To characterize release of incorporated BMP-2, samples will be incubated in DMEM for 14 days. Every 24 hr, media will be refreshed and radioactivity in solution will be measured. The release will take place over multiple weeks in solution with linear release kinetics. Release duration will be controlled by varying the coating thickness. Release rate may be controlled by the concentration of growth factor in the CaP layer. A broad range of total BMP-2 release from scaffolds will be demonstrated. The total amount of protein released will be dictated by the amount of BMP-2 included during mineralization (10-1000 nM). A high level of controlled release of BMP-2 incorporation/release will be demonstrated.

EXAMPLE 6

Figure 6:
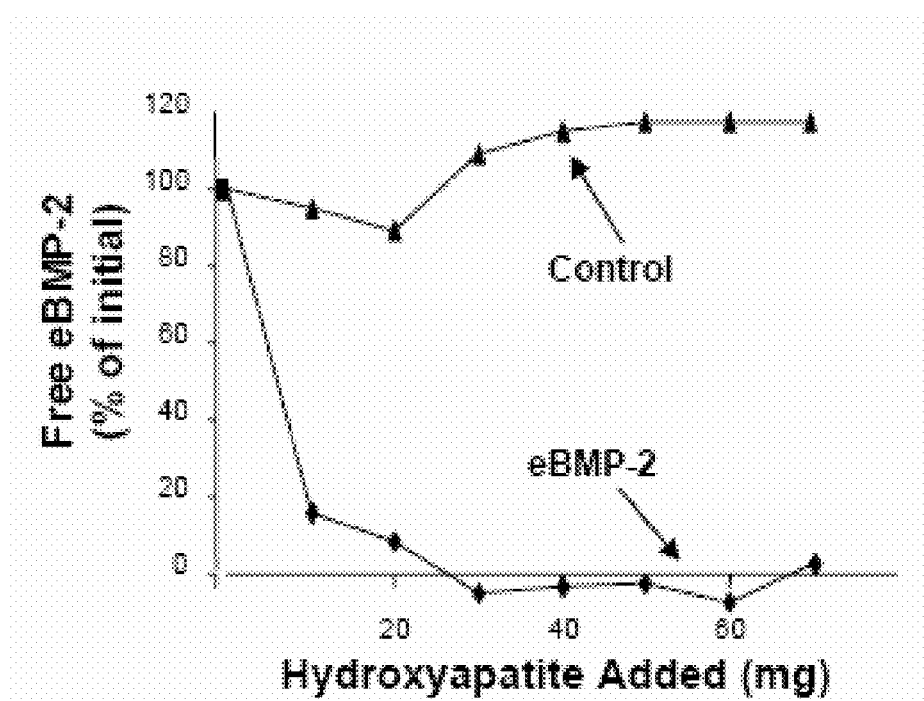
FIG. 6 is a graph showing controlled release of engineered BMP-2 (eBMP-2) from a layer of hydroxyapatite coated on a bioresorbable interference bone screw constructed from poly (L-lactide), whereby the data demonstrate that growth factor, such as eBMP-2, binds to the hydroxyapatite mineral in solution.
Figure 7:
FIG. 7 is a stem cell-based bioactivity assay −BMP-2.
Figure 8:
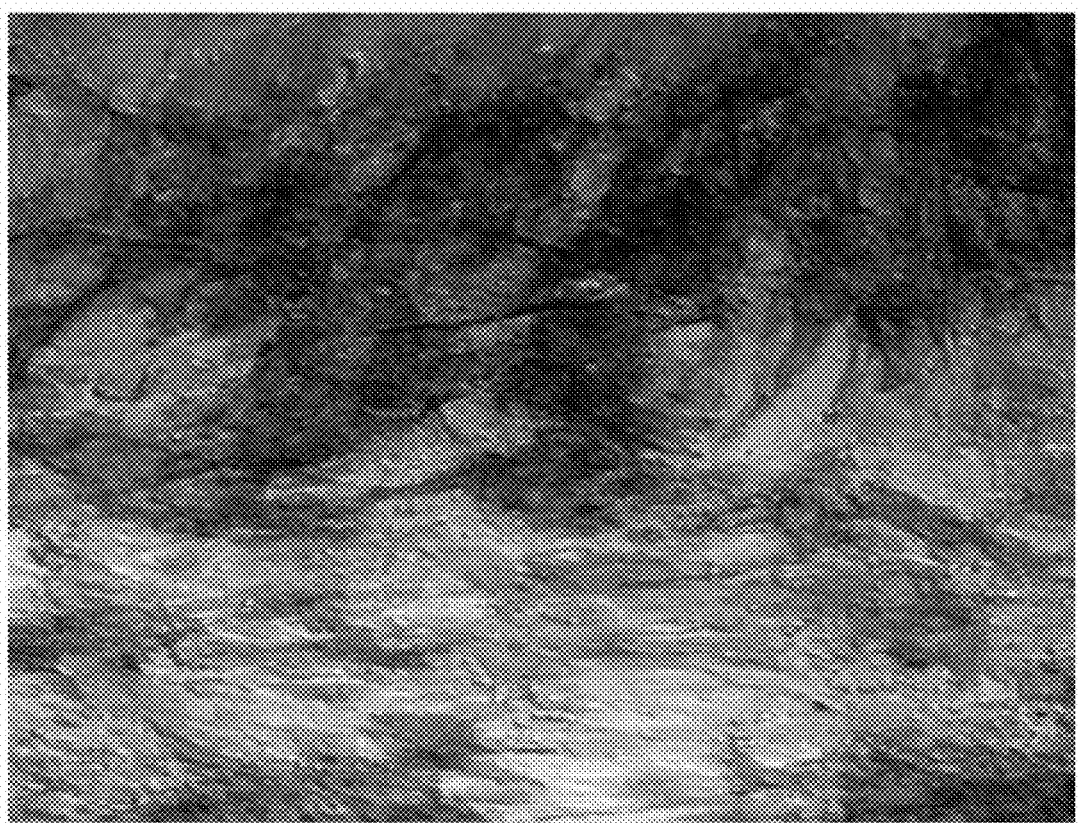
FIG. 8 is a stem cell-based bioactivity assay +BMP-2.
Figure 9:
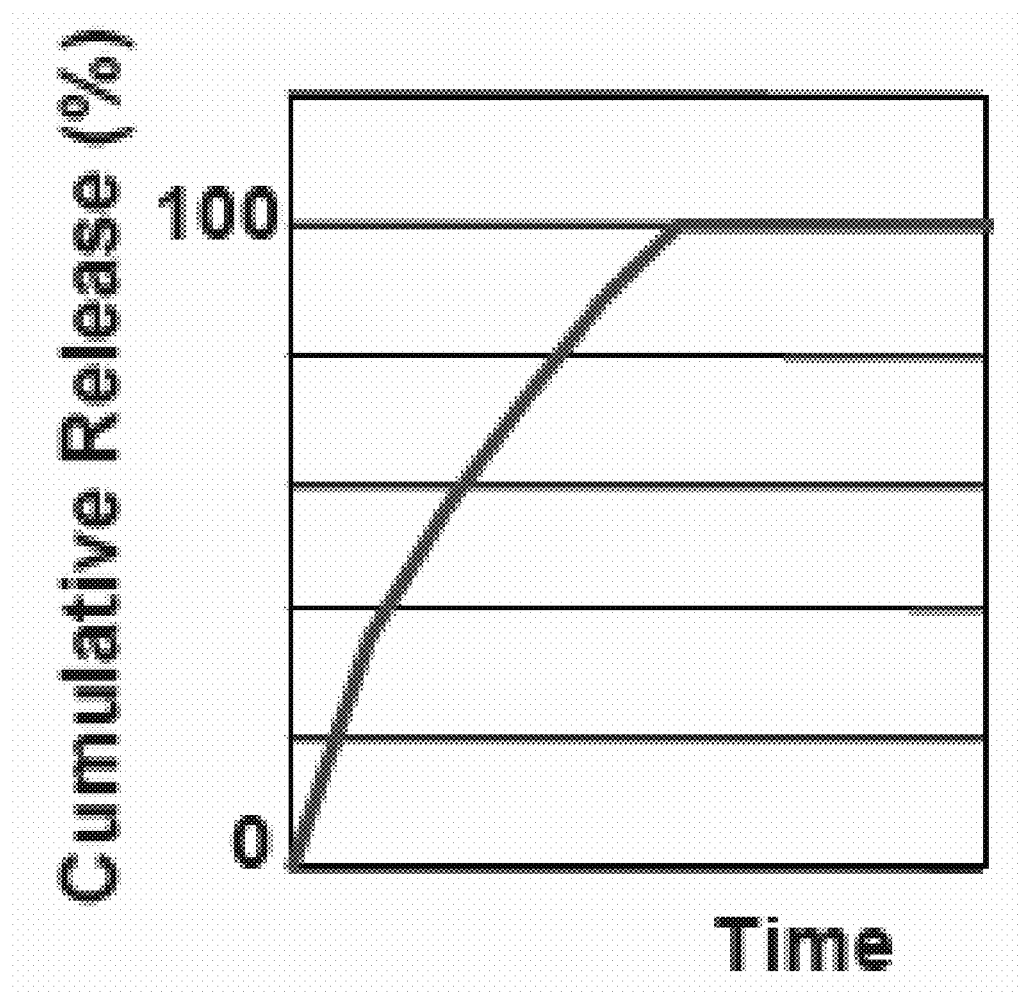
FIG. 9 is a graph illustrating the cumulative controlled release of growth factor from the hydroxyapatite layer.

Characterization of BMP bioactivity. A well-defined and biologically relevant assay will be used to confirm the biological activity of BMP-2 after release from the mineral coatings. Promotion of osteogenic differentiation is a key function of BMP-2. Osteogenic induction of the mouse fibroblast cell line C3H10T1/2 by BMP-2 is well-characterized. Therefore, a C3H10T1/2 cell-based biological activity assay will be used to characterize soluble BMP-2 released from mineralized PLLA screws. (See, FIG. 6). The cells will be exposed to 0.1-100 ng/ml BMP-2 released from mineral layers. Alkaline phosphatase upregulation, a hallmark of osteogenic induction, will be measured. The results will be compared to a standard curve that relates soluble BMP-2 concentrations (not released from coatings) to alkaline phosphatase upregulation, which will provide the effective activity of released BMP-2. The activity of the release BMP-2 will not be substantially affected by mineral binding and release, perhaps because BMPs incorporate within calcium phosphate minerals under normal conditions in vivo.

EXAMPLE 7

Characterization of efficacy of biologically active bone screws in ligament fixation. Testing of BMP-2-loaded interference screws in a tibial bone tunnel in sheep. Sheep will be anesthetized in accordance with RARC-approved surgical protocol. The tendonous origin of the common extensor muscles will be released from the femur and placed in a tunnel drilled transversely in the proximal tibial metaphysis. The tunnel and tendon sizes range from 7-8 mm, which is nearly identical in scale to the human tunnels drilled in the tibia and femur for reconstruction of the ACL. This allows use of human screw implants to fix the graft in place enhancing the clinical relevance. The biologically active implant will release 90 μg BMP-2 over a 6 week timeframe. It will be placed in one stifle, and an identical implant without BMP-2 will be placed in the other stifle.

Characterization of healing. Healing will initially be assessed at 6 weeks postoperative by ACT, which accurately measures tunnel size and records any degree of tunnel expansion. Histological analysis will evaluate the quality of the bone-tendon interface, and the effects of the bioactive screw on adjacent bone. Specifically, bone formation will be analyzed, and the nature of the bone-tendon interface in the tunnel via H&E staining. Width and properties of the "interface zone" between the tendon and native bone will be of interest, and such is indicative of the quality of graft-bone healing (i.e., a wide fibrous or empty interface indicates poor healing).

EXAMPLE 8

Sequence Listings.
Set forth below in the Sequence Listing are the DNA (SEQ ID NO: 1) and derived amino acid sequence (SEQ ID NO: 2) of human BMP-2 from lambda U20S-39, ATCC #40345.

SEQ ID NO: 1, Length: 1607, Type: DNA, Organism: *Homo Sapiens*, Name/Key: CDS, Location: (356).(1543)

SEQ ID NO: 2, Length: 396, Type: PRT, Organism: *Homo Sapiens*.

Set forth below are the DNA (SEQ ID NO: 3) and derived amino acid sequence (SEQ ID NO: 4) of human BMP-4 from lambda U20S-3, ATCC #40342.

SEQ ID NO: 3, Length: 1954, Type: DNA, Organism: *Homo Sapiens*, Name/Key: CDS, Location: (403).(1626)

SEQ ID NO: 4, Length: 408, Type: PRT, Organism: *Homo Sapiens*.

EXAMPLE 9

Other synthetic peptides useful as growth factor in the instant invention are disclosed in Saito A, et al., "Activation of osteo-progenitor cells by a novel synthetic peptide derived from the bone morphogenetic protein-2 knuckle epitope," *Biochimica et Biophysica Acta* 2003, 1651:60-67, incorporated herein by reference as if set forth in its entirety. Specifically, peptides P2, P3 and P4 shown in Table 1 are useful growth factors to be chemically bound within the hydroxyapatite coating of the instant invention. The amino acid sequence of such BMP-2 derived peptides (the amino acid residues different from the sequence of hBMP-2 are shown in bold) information for P2, P3 and P4 is set forth below and defined as SEQ ID NOS: 5, 6 and 7, respectively.

```
SEQ ID NO: 5
NSVNS KIPKA CSVPT ELSAI STLYL
{hBMP-2: 68-92 (C79S, M89T)}

SEQ ID NO: 6
NSVNS KIPKA SSVPT ELSAI STLYL
{hBMP-2: 68-92 (C78, 79S, M89T)}

SEQ ID NO: 7
KIPKA SSVPT ELSAI STLYL
{hBMP-2: 73-92 (C78, 79S, M89T)}
```

EXAMPLE 10

The following biomimetic hydroxyapatite-binding tag sequences are useful within a polypeptide (such as the hBMP-2 molecules having SEQ ID NO: 2, amino acids 299-396 of SEQ ID NO: 2, amino acids 283-396 of SEQ ID NO: 2, SEQ ID NO: 5, SEQ ID NO: 6 or SEQ ID NO: 7 or hBMP-4 molecules having SEQ ID NO: 4, amino acids 311-408 of SEQ ID NO: 4 or amino acids 293-408 of SEQ ID NO: 4) for covalently binding to hydroxyapatite.

```
SEQ ID NO: 8      AAAAγEPRRγEVAγEL
SEQ ID NO: 9      AAAAγEPRRAVAγEL
SEQ ID NO: 10     AAAAγEPRRAVAAL
SEQ ID NO: 11     AAAAEPRREVAEL
SEQ ID NO: 12     AAAAAPRREVAEL
SEQ ID NO: 13     AAAAAPRRAVAEL
```

EXAMPLE 11

The tag sequences shown in SEQ ID NOS: 8-13 are covalently bonded to the e-BNP-2 (i.e., SEQ ID NO: 7) to produce the following sequences.

```
SEQ ID NO: 14 KIPKASSVPTELSAISTLYLAAAAEPRREVAEL
SEQ ID NO: 15 KIPKASSVPTELSAISTLYLAAAAEPRRAVAEL
SEQ ID NO: 16 KIPKASSVPTELSAISTLYLAAAAEPRRAVAAL
SEQ ID NO: 17 KIPKASSVPTELSAISTLYLAAAAγEPRRγEVAγEL
SEQ ID NO: 18 KIPKASSVPTELSAISTLYLAAAAγEPRRAVAγEL
SEQ ID NO: 19 KIPKASSVPTELSAISTLYLAAAAγEPRRAVAAL
SEQ ID NO: 20 KIPKASSVPTELSAISTLYL
```

We claim:

1. An implantable scaffold comprising a bioresorbable substrate, the implantable scaffold made by a method comprising:
   surface hydrolyzing the bioresorbable substrate under alkaline conditions; and
   incubating the hydrolyzed bioresorbable substrate in modified simulated body fluid containing calcium ions, phosphate ions and growth factor;
   wherein hydroxyapatite grows on the bioresorbable substrate, the hydroxyapatite having one or more active biopharmaceutical growth factors chemically bonded therein.

2. The implantable scaffold of claim 1, wherein the bioresorbable substrate is constructed from a poly(α-hydroxy ester).

3. The implantable scaffold of claim 2, wherein the poly(α-hydroxy ester) is a member selected from the group consisting of poly(L-lactide), poly (lactide-co-glycolide) and poly(ε-caprolactone).

4. The implantable scaffold of claim 3, wherein the poly(α-hydroxy ester) is poly(L-lactide).

5. The method of claim 4, wherein the bioresorbable substrate is an interference screw.

6. The implantable scaffold of claim 1, wherein the active biopharmaceutical growth factor includes a first polypeptide selected from the group consisting of SEQ ID NO: 2, amino acids 299-396 of SEQ ID NO: 2, amino acids 283-396 of SEQ ID NO: 2, SEQ ID NO: 5, SEQ ID NO: 6, SEQ ID NO: 7, SEQ ID NO: 14, SEQ ID NO: 15, SEQ ID NO: 16, SEQ ID NO: 17, SEQ ID NO: 18 and SEQ ID NO: 19.

7. The implantable scaffold of claim 6, wherein the active biopharmaceutical growth factors includes a second polypeptide selected from the group consisting of SEQ ID NO: 4, amino acids 311-408 of SEQ ID NO: 4, and amino acids 293-408 of SEQ ID NO: 4.

8. An interference screw comprising a bioresorbable substrate, the interference screw made by a method comprising:
   surface hydrolyzing the bioresorbable substrate under alkaline conditions; and
   incubating the hydrolyzed bioresorbable substrate in modified simulated body fluid containing calcium ions, phosphate ions and growth factor;
   wherein hydroxyapatite grows on the bioresorbable substrate, the hydroxyapatite having one or more active biopharmaceutical growth factors chemically bonded therein.

9. The interference screw of claim 8, wherein the bioresorbable substrate is constructed from a poly(α-hydroxy ester).

10. The interference screw of claim 9, wherein the poly(α-hydroxy ester) is a member selected from the group consisting of poly(L-lactide), poly (lactide-co-glycolide) and poly (ε-caprolactone).

11. The interference screw of claim 10, wherein the poly(α-hydroxy ester) is poly(L-lactide).

12. The interference screw of claim 8, wherein the active biopharmaceutical growth factor includes a first polypeptide selected from the group consisting of SEQ ID NO: 2, amino acids 299-396 of SEQ ID NO: 2, amino acids 283-396 of SEQ ID NO: 2, SEQ ID NO: 5, SEQ ID NO: 6, SEQ ID NO: 7, SEQ ID NO: 14, SEQ ID NO: 15, SEQ ID NO: 16, SEQ ID NO: 17, SEQ ID NO: 18 and SEQ ID NO: 19.

13. The interference screw of claim 12, wherein the active biopharmaceutical growth factor includes a second polypeptide selected from the group consisting of SEQ ID NO: 4, amino acids 311-408 of SEQ ID NO: 4, and amino acids 293-408 of SEQ ID NO: 4.

14. A method of treating or reducing tunnel widening in the tibia or femur of a patient attendant to reconstruction of the anterior cruciate ligament in a human comprising controlled delivery of growth factor from the interference screw of claim 8 to a tendon graft secured in the tunnel by the interference screw.

15. A method of reconstructing anterior cruciate ligament in a human comprising:
   removing damaged ligament;
   drilling a tunnel through the tibia and femur;
   inserting a graft selected from the group consisting of hamstring tendon and patellar tendon through the tibia tunnel and the femur tunnel; and
   affixing the graft to tibia and femur tunnels with the interference screw of claim 8.

16. An orthopedic implant for controlled delivery of one or more active biopharmaceutical growth factors comprising: a bioresorbable scaffold; and a bioactive coating, wherein one or more active biopharmaceutical growth factors are chemically bonded within a coating comprising calcium and phosphate.

17. The orthopedic implant of claim 16, wherein the bioresorbable scaffold is constructed from a poly(α-hydroxy ester).

18. The orthopedic implant of claim 17, wherein the poly(α-hydroxy ester) is a member selected from the group consisting of poly(L-lactide), poly(lactide-co-glycolide) and poly(ε-caprolactone).

19. The orthopedic implant of claim 17, wherein the poly (α-hydroxy ester) is poly(L-lactide).

20. The orthopedic implant of claim 16, wherein the scaffold is a member selected from the group consisting of an arrow, barb, tack, anchor, nail, pin, screw, staple and plate.

21. The orthopedic implant of claim 16, wherein the bioactive coating comprises hydroxyapatite, and wherein the active biopharmaceutical growth factors comprise a first polypeptide selected from the group consisting of human bone morphogenetic protein-2 and a functional derivative thereof.

22. The orthopedic implant of claim 21, wherein the first polypeptide is selected from the group consisting of SEQ ID NO: 2, amino acids 299-396 of SEQ ID NO: 2, amino acids 283-396 of SEQ ID NO: 2, SEQ ID NO: 5, SEQ ID NO: 6, SEQ ID NO: 7, SEQ ID NO: 14, SEQ ID NO: 15, SEQ ID NO: 16, SEQ ID NO: 17, SEQ ID NO: 18 and SEQ ID NO: 19.

23. The orthopedic implant of claim 22, further comprising a second polypeptide selected from the group consisting of human bone morphogenetic protein-4 having the sequence of SEQ ID NO: 4, amino acids 311-408 of SEQ ID NO: 4, and amino acids 293-408 of SEQ ID NO: 4.

24. A method of growing hydroxyapatite on a bioresorbable substrate, the hydroxyapatite having one or more active biopharmaceutical growth factors chemically bonded therein, comprising: surface hydrolyzing the bioresorbable substrate under alkaline conditions; and incubating the hydrolyzed bioresorbable substrate in modified simulated body fluid containing calcium ions, phosphate ions and growth factor, wherein hydroxyapatite grows on the bioresorbable substrate, the hydroxyapatite having one or more active biopharmaceutical growth factors chemically bonded therein.

25. An orthopedic implant for controlled delivery of growth factor comprising: a bioresorbable scaffold; and a bioactive coating, wherein a human bone morphogenetic protein-2 molecule is chemically bonded within a coating comprising calcium and phosphate.

* * * * *

SEQUENCE LISTING

<160> NUMBER OF SEQ ID NOS: 20

<210> SEQ ID NO 1
<211> LENGTH: 1607
<212> TYPE: DNA
<213> ORGANISM: Homo sapiens
<220> FEATURE:
<221> NAME/KEY: CDS
<222> LOCATION: (356)..(1543)

<400> SEQUENCE: 1

```
gtcgactcta gagtgtgtgt cagcacttgg ctggggactt cttgaacttg cagggagaat    60
aacttgcgca ccccactttg cgccggtgcc tttgccccag cggagcctgc ttcgccatct   120
ccgagcccca ccgcccctcc actcctcggc cttgcccgac actgagacgc tgttcccagc   180
gtgaaaagag agactgcgcg gccggcaccc gggagaagga ggaggcaaag aaaaggaacg   240
gacattcggt ccttgcgcca ggtcctttga ccagagtttt tccatgtgga cgctctttca   300
atggacgtgt ccccgcgtgc ttcttagacg gactgcggtc tcctaaaggt cgacc atg    358
                                                              Met
                                                               1 gtg gcc ggg acc cgc tgt ctt cta gcg ttg ctg ctt ccc cag gtc ctc    406
Val Ala Gly Thr Arg Cys Leu Leu Ala Leu Leu Leu Pro Gln Val Leu
         5                  10                  15 ctg ggc ggc gcg gct ggc ctc gtt ccg gag ctg ggc cgc agg aag ttc    454
Leu Gly Gly Ala Ala Gly Leu Val Pro Glu Leu Gly Arg Arg Lys Phe
     20                  25                  30 gcg gcg gcg tcg tcg ggc cgc ccc tca tcc cag ccc tct gac gag gtc    502
Ala Ala Ala Ser Ser Gly Arg Pro Ser Ser Gln Pro Ser Asp Glu Val
 35                  40                  45 ctg agc gag ttc gag ttg cgg ctg ctc agc atg ttc ggc ctg aaa cag    550
Leu Ser Glu Phe Glu Leu Arg Leu Leu Ser Met Phe Gly Leu Lys Gln
 50                  55                  60                  65 aga ccc acc ccc agc agg gac gcc gtg gtg ccc ccc tac atg cta gac    598
Arg Pro Thr Pro Ser Arg Asp Ala Val Val Pro Pro Tyr Met Leu Asp
             70                  75                  80 ctg tat cgc agg cac tca ggt cag ccg ggc tca ccc gcc cca gac cac    646
Leu Tyr Arg Arg His Ser Gly Gln Pro Gly Ser Pro Ala Pro Asp His
         85                  90                  95 cgg ttg gag agg gca gcc agc cga gcc aac act gtg cgc agc ttc cac    694
Arg Leu Glu Arg Ala Ala Ser Arg Ala Asn Thr Val Arg Ser Phe His
    100                 105                 110 cat gaa gaa tct ttg gaa gaa cta cca gaa acg agt ggg aaa aca acc    742
His Glu Glu Ser Leu Glu Glu Leu Pro Glu Thr Ser Gly Lys Thr Thr
115                 120                 125 cgg aga ttc ttc ttt aat tta agt tct atc ccc acg gag gag ttt atc    790
Arg Arg Phe Phe Phe Asn Leu Ser Ser Ile Pro Thr Glu Glu Phe Ile
130                 135                 140                 145 acc tca gca gag ctt cag gtt ttc cga gaa cag atg caa gat gct tta    838
Thr Ser Ala Glu Leu Gln Val Phe Arg Glu Gln Met Gln Asp Ala Leu
                150                 155                 160 gga aac aat agc agt ttc cat cac cga att aat att tat gaa atc ata    886
Gly Asn Asn Ser Ser Phe His His Arg Ile Asn Ile Tyr Glu Ile Ile
            165                 170                 175 aaa cct gca aca gcc aac tcg aaa ttc ccc gtg acc aga ctt ttg gac    934
Lys Pro Ala Thr Ala Asn Ser Lys Phe Pro Val Thr Arg Leu Leu Asp
        180                 185                 190 acc agg ttg gtg aat cag aat gca agc agg tgg gaa agt ttt gat gtc    982
Thr Arg Leu Val Asn Gln Asn Ala Ser Arg Trp Glu Ser Phe Asp Val
    195                 200                 205
```

```
acc ccc gct gtg atg cgg tgg act gca cag gga cac gcc aac cat gga    1030
Thr Pro Ala Val Met Arg Trp Thr Ala Gln Gly His Ala Asn His Gly
210                 215                 220                 225 ttc gtg gtg gaa gtg gcc cac ttg gag gag aaa caa ggt gtc tcc aag    1078
Phe Val Val Glu Val Ala His Leu Glu Glu Lys Gln Gly Val Ser Lys
                230                 235                 240 aga cat gtt agg ata agc agg tct ttg cac caa gat gaa cac agc tgg    1126
Arg His Val Arg Ile Ser Arg Ser Leu His Gln Asp Glu His Ser Trp
            245                 250                 255 tca cag ata agg cca ttg cta gta act ttt ggc cat gat gga aaa ggg    1174
Ser Gln Ile Arg Pro Leu Leu Val Thr Phe Gly His Asp Gly Lys Gly
        260                 265                 270 cat cct ctc cac aaa aga gaa aaa cgt caa gcc aaa cac aaa cag cgg    1222
His Pro Leu His Lys Arg Glu Lys Arg Gln Ala Lys His Lys Gln Arg
    275                 280                 285 aaa cgc ctt aag tcc agc tgt aag aga cac cct ttg tac gtg gac ttc    1270
Lys Arg Leu Lys Ser Ser Cys Lys Arg His Pro Leu Tyr Val Asp Phe
290                 295                 300                 305 agt gac gtg ggg tgg aat gac tgg att gtg gct ccc ccg ggg tat cac    1318
Ser Asp Val Gly Trp Asn Asp Trp Ile Val Ala Pro Pro Gly Tyr His
                310                 315                 320 gcc ttt tac tgc cac gga gaa tgc cct ttt cct ctg gct gat cat ctg    1366
Ala Phe Tyr Cys His Gly Glu Cys Pro Phe Pro Leu Ala Asp His Leu
            325                 330                 335 aac tcc act aat cat gcc att gtt cag acg ttg gtc aac tct gtt aac    1414
Asn Ser Thr Asn His Ala Ile Val Gln Thr Leu Val Asn Ser Val Asn
        340                 345                 350 tct aag att cct aag gca tgc tgt gtc ccg aca gaa ctc agt gct atc    1462
Ser Lys Ile Pro Lys Ala Cys Cys Val Pro Thr Glu Leu Ser Ala Ile
    355                 360                 365 tcg atg ctg tac ctt gac gag aat gaa aag gtt gta tta aag aac tat    1510
Ser Met Leu Tyr Leu Asp Glu Asn Glu Lys Val Val Leu Lys Asn Tyr
370                 375                 380                 385 cag gac atg gtt gtg gag ggt tgt ggg tgt cgc tagtacagca aaattaaata  1563
Gln Asp Met Val Val Glu Gly Cys Gly Cys Arg
                390                 395 cataaatata tatatatata tatattttag aaaaaagaaa aaaa                   1607

<210> SEQ ID NO 2
<211> LENGTH: 396
<212> TYPE: PRT
<213> ORGANISM: Homo sapiens

<400> SEQUENCE: 2

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
        50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110
```

His His Glu Glu Ser Leu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 3
<211> LENGTH: 1954
<212> TYPE: DNA
<213> ORGANISM: Homo sapiens
<220> FEATURE:
<221> NAME/KEY: CDS
<222> LOCATION: (403)..(1626)

<400> SEQUENCE: 3
ctctagaggg cagaggagga gggagggagg gaaggagcgc ggagcccggc ccggaagcta      60
ggtgagtgtg gcatccgagc tgagggacgc gagcctgaga cgccgctgct gctccggctg     120
agtatctagc ttgtctcccc gatgggattc ccgtccaagc tatctcgagc ctgcagcgcc     180
acagtccccg gccctcgccc aggttcactg caaccgttca gaggtcccca ggagctgctg     240
ctggcgagcc cgctactgca gggacctatg gagccattcc gtagtgccat cccgagcaac     300
gcactgctgc agcttccctg agcctttcca gcaagtttgt tcaagattgg ctgtcaagaa     360
tcatggactg ttattatatg ccttgttttc tgtcaagaca cc atg att cct ggt        414
                                                Met Ile Pro Gly
                                                  1

| | | |
|---|---|---|
| aac cga atg ctg atg gtc gtt tta tta tgc caa gtc ctg cta gga ggc<br>Asn Arg Met Leu Met Val Val Leu Leu Cys Gln Val Leu Leu Gly Gly<br>5                            10                      15                  20 | | 462 |
| gcg agc cat gct agt ttg ata cct gag acg ggg aag aaa aaa gtc gcc<br>Ala Ser His Ala Ser Leu Ile Pro Glu Thr Gly Lys Lys Lys Val Ala<br>                       25                      30                      35 | | 510 |
| gag att cag ggc cac gcg gga gga cgc cgc tca ggg cag agc cat gag<br>Glu Ile Gln Gly His Ala Gly Gly Arg Arg Ser Gly Gln Ser His Glu<br>            40                      45                      50 | | 558 |
| ctc ctg cgg gac ttc gag gcg aca ctt ctg cag atg ttt ggg ctg cgc<br>Leu Leu Arg Asp Phe Glu Ala Thr Leu Leu Gln Met Phe Gly Leu Arg<br>        55                      60                      65 | | 606 |
| cgc cgc ccg cag cct agc aag agt gcc gtc att ccg gac tac atg cgg<br>Arg Arg Pro Gln Pro Ser Lys Ser Ala Val Ile Pro Asp Tyr Met Arg<br>70                            75                      80 | | 654 |
| gat ctt tac cgg ctt cag tct ggg gag gag gag gaa gag cag atc cac<br>Asp Leu Tyr Arg Leu Gln Ser Gly Glu Glu Glu Glu Glu Gln Ile His<br>85                          90                      95                    100 | | 702 |
| agc act ggt ctt gag tat cct gag cgc ccg gcc agc cgg gcc aac acc<br>Ser Thr Gly Leu Glu Tyr Pro Glu Arg Pro Ala Ser Arg Ala Asn Thr<br>                       105                    110                    115 | | 750 |
| gtg agg agc ttc cac cac gaa gaa cat ctg gag aac atc cca ggg acc<br>Val Arg Ser Phe His His Glu Glu His Leu Glu Asn Ile Pro Gly Thr<br>                  120                    125                    130 | | 798 |
| agt gaa aac tct gct ttt cgt ttc ctc ttt aac ctc agc agc atc cct<br>Ser Glu Asn Ser Ala Phe Arg Phe Leu Phe Asn Leu Ser Ser Ile Pro<br>             135                    140                    145 | | 846 |
| gag aac gag gtg atc tcc tct gca gag ctt cgg ctc ttc cgg gag cag<br>Glu Asn Glu Val Ile Ser Ser Ala Glu Leu Arg Leu Phe Arg Glu Gln<br>150                         155                    160 | | 894 |
| gtg gac cag ggc cct gat tgg gaa agg ggc ttc cac cgt ata aac att<br>Val Asp Gln Gly Pro Asp Trp Glu Arg Gly Phe His Arg Ile Asn Ile<br>165                       170                    175                    180 | | 942 |
| tat gag gtt atg aag ccc cca gca gaa gtg gtg cct ggg cac ctc atc<br>Tyr Glu Val Met Lys Pro Pro Ala Glu Val Val Pro Gly His Leu Ile<br>                          185                    190                    195 | | 990 |
| aca cga cta ctg gac acg aga ctg gtc cac cac aat gtg aca cgg tgg<br>Thr Arg Leu Leu Asp Thr Arg Leu Val His His Asn Val Thr Arg Trp<br>             200                    205                    210 | | 1038 |
| gaa act ttt gat gtg agc cct gcg gtc ctt cgc tgg acc cgg gag aag<br>Glu Thr Phe Asp Val Ser Pro Ala Val Leu Arg Trp Thr Arg Glu Lys<br>                  215                    220                    225 | | 1086 |
| cag cca aac tat ggg cta gcc att gag gtg act cac ctc cat cag act<br>Gln Pro Asn Tyr Gly Leu Ala Ile Glu Val Thr His Leu His Gln Thr<br>230                       235                    240 | | 1134 |
| cgg acc cac cag ggc cag cat gtc agg att agc cga tcg tta cct caa<br>Arg Thr His Gln Gly Gln His Val Arg Ile Ser Arg Ser Leu Pro Gln<br>245                       250                    255                    260 | | 1182 |
| ggg agt ggg aat tgg gcc cag ctc cgg ccc ctc ctg gtc acc ttt ggc<br>Gly Ser Gly Asn Trp Ala Gln Leu Arg Pro Leu Leu Val Thr Phe Gly<br>                       265                    270                    275 | | 1230 |
| cat gat ggc cgg ggc cat gcc ttg acc cga cgc cgg agg gcc aag cgt<br>His Asp Gly Arg Gly His Ala Leu Thr Arg Arg Arg Arg Ala Lys Arg<br>            280                    285                    290 | | 1278 |
| agc cct aag cat cac tca cag cgg gcc agg aag aag aat aag aac tgc<br>Ser Pro Lys His His Ser Gln Arg Ala Arg Lys Lys Asn Lys Asn Cys<br>                  295                    300                    305 | | 1326 |
| cgg cgc cac tcg ctc tat gtg gac ttc agc gat gtg ggc tgg aat gac<br>Arg Arg His Ser Leu Tyr Val Asp Phe Ser Asp Val Gly Trp Asn Asp<br>310                         315                    320 | | 1374 |

```
tgg att gtg gcc cca cca ggc tac cag gcc ttc tac tgc cat ggg gac      1422
Trp Ile Val Ala Pro Pro Gly Tyr Gln Ala Phe Tyr Cys His Gly Asp
325                 330                 335                 340 tgc ccc ttt cca ctg gct gac cac ctc aac tca acc aac cat gcc att      1470
Cys Pro Phe Pro Leu Ala Asp His Leu Asn Ser Thr Asn His Ala Ile
                345                 350                 355 gtg cag acc ctg gtc aat tct gtc aat tcc agt atc ccc aaa gcc tgt      1518
Val Gln Thr Leu Val Asn Ser Val Asn Ser Ser Ile Pro Lys Ala Cys
            360                 365                 370 tgt gtg ccc act gaa ctg agt gcc atc tcc atg ctg tac ctg gat gag      1566
Cys Val Pro Thr Glu Leu Ser Ala Ile Ser Met Leu Tyr Leu Asp Glu
        375                 380                 385 tat gat aag gtg gta ctg aaa aat tat cag gag atg gta gta gag gga      1614
Tyr Asp Lys Val Val Leu Lys Asn Tyr Gln Glu Met Val Val Glu Gly
    390                 395                 400 tgt ggg tgc cgc tgagatcagg cagtccttga ggatagacag atatacacac          1666
Cys Gly Cys Arg
405 cacacacaca caccacatac accacacaca cacgttccca tccactcacc cacacactac    1726 acagactgct tccttatagc tggactttta tttaaaaaaa aaaaaaaaaa aatggaaaaa    1786 atccctaaac attcaccttg accttattta tgactttacg tgcaaatgtt ttgaccatat    1846 tgatcatata ttttgacaaa atatatttat aactacgtat taaagaaaaa aaataaaatg    1906 agtcattatt ttaaaaaaaa aaaaaaaact ctagagtcga cggaattc                 1954

<210> SEQ ID NO 4
<211> LENGTH: 408
<212> TYPE: PRT
<213> ORGANISM: Homo sapiens

<400> SEQUENCE: 4

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
```

```
                195                 200                 205
Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 5
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 5

Asn Ser Val Asn Ser Lys Ile Pro Lys Ala Cys Ser Val Pro Thr Glu
1               5                   10                  15

Leu Ser Ala Ile Ser Thr Leu Tyr Leu
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 6

Asn Ser Val Asn Ser Lys Ile Pro Lys Ala Ser Ser Val Pro Thr Glu
1               5                   10                  15

Leu Ser Ala Ile Ser Thr Leu Tyr Leu
            20                  25

<210> SEQ ID NO 7
<211> LENGTH: 20
<212> TYPE: PRT
<213> ORGANISM: Artificial Sequence
<220> FEATURE:
<223> OTHER INFORMATION: Synthetic polypeptide
```

-continued

```
<400> SEQUENCE: 7

Lys Ile Pro Lys Ala Ser Ser Val Pro Thr Glu Leu Ser Ala Ile Ser
1               5                   10                  15

Thr Leu Tyr Leu
            20

<210> SEQ ID NO 8
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Gamma carboxylated glutamic acid
<220> FEATURE:
<221> NAME/KEY: MISC_FEATURE
<222> LOCATION: (9)..(9)
<223> OTHER INFORMATION: Gamma carboxylated glutamic acid
<220> FEATURE:
<221> NAME/KEY: MISC_FEATURE
<222> LOCATION: (12)..(12)
<223> OTHER INFORMATION: Gamma carboxylated glutamic acid

<400> SEQUENCE: 8

Ala Ala Ala Ala Glu Pro Arg Arg Glu Val Ala Glu Leu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Gamma carboxylated glutamic acid
<220> FEATURE:
<221> NAME/KEY: MISC_FEATURE
<222> LOCATION: (12)..(12)
<223> OTHER INFORMATION: Gamma carboxylated glutamic acid

<400> SEQUENCE: 9

Ala Ala Ala Ala Glu Pro Arg Arg Ala Val Ala Glu Leu
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Gamma carboxylated glutamic acid

<400> SEQUENCE: 10

Ala Ala Ala Ala Glu Pro Arg Arg Ala Val Ala Ala Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic polypeptide
```

```
<400> SEQUENCE: 11

Ala Ala Ala Ala Glu Pro Arg Arg Glu Val Ala Glu Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 12

Ala Ala Ala Ala Ala Pro Arg Arg Glu Val Ala Glu Leu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 13

Ala Ala Ala Ala Ala Pro Arg Arg Ala Val Ala Glu Leu
1               5                   10

<210> SEQ ID NO 14
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 14

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Glu Val Ala Glu
            20                  25                  30

Leu

<210> SEQ ID NO 15
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 15

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Ala Val Ala Glu
            20                  25                  30

Leu

<210> SEQ ID NO 16
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 16

Lys Ile Pro Lys Ala Ser Ser Val Pro Thr Glu Leu Ser Ala Ile Ser
1               5                   10                  15
```

```
Thr Leu Tyr Leu Ala Ala Ala Ala Glu Pro Arg Arg Ala Val Ala Ala
            20                  25                  30

Leu

<210> SEQ ID NO 17
<211> LENGTH: 33
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (25)..(25)
<223> OTHER INFORMATION: Gamma carboxylated glutamic acid
<220> FEATURE:
<221> NAME/KEY: MISC_FEATURE
<222> LOCATION: (29)..(29)
<223> OTHER INFORMATION: Gamma carboxylated glutamic acid
<220> FEATURE:
<221> NAME/KEY: MISC_FEATURE
<222> LOCATION: (32)..(32)
<223> OTHER INFORMATION: Gamma carboxylated glutamic acid

<400> SEQUENCE: 17

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Glu Val Ala Glu
            20                  25                  30

Leu

<210> SEQ ID NO 18
<211> LENGTH: 33
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (25)..(25)
<223> OTHER INFORMATION: Gamma carboxylated glutamic acid
<220> FEATURE:
<221> NAME/KEY: MISC_FEATURE
<222> LOCATION: (32)..(32)
<223> OTHER INFORMATION: Gamma carboxylated glutamic acid

<400> SEQUENCE: 18

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Ala Val Ala Glu
            20                  25                  30

Leu

<210> SEQ ID NO 19
<211> LENGTH: 33
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (25)..(25)
<223> OTHER INFORMATION: Gamma carboxylated glutamic acid

<400> SEQUENCE: 19

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Ala Val Ala Ala
            20                  25                  30
```

-continued

```
Leu

<210> SEQ ID NO 20
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 20

Lys Ile Pro Lys Ala Ser Ser Val Pro Thr Glu Leu Ser Ala Ile Ser
1               5                   10                  15

Thr Leu Tyr Leu
            20
```